US010533979B2

(12) United States Patent
Mori et al.

(10) Patent No.: US 10,533,979 B2
(45) Date of Patent: Jan. 14, 2020

(54) METHOD OF AND APPARATUS FOR FORMULATING MULTICOMPONENT DRUG

(71) Applicant: TSUMURA & CO., Minato-ku, Tokyo (JP)

(72) Inventors: Yoshikazu Mori, Ibaraki (JP); Keiichi Noda, Ibaraki (JP)

(73) Assignee: Tsumura & Co., Tokyo (JP)

( * ) Notice: Subject to any disclaimer, the term of this patent is extended or adjusted under 35 U.S.C. 154(b) by 338 days.

(21) Appl. No.: 15/269,644

(22) Filed: Sep. 19, 2016

(65) Prior Publication Data

US 2017/0010245 A1 Jan. 12, 2017

Related U.S. Application Data

(63) Continuation-in-part of application No. 13/806,683, filed as application No. PCT/JP2012/003612 on May 31, 2012, now abandoned.

(30) Foreign Application Priority Data

Jun. 1, 2011 (JP) .................................. 2011-123847

(51) Int. Cl.
*G01N 30/86* (2006.01)
*G01N 30/88* (2006.01)
*G16C 20/20* (2019.01)

(52) U.S. Cl.
CPC ......... *G01N 30/8686* (2013.01); *G01N 30/88* (2013.01); *G16C 20/20* (2019.02); *G01N 2030/8886* (2013.01)

(58) Field of Classification Search
CPC ........... G01N 30/8675; G01N 30/8686; G01N 30/74; G01N 30/8679; G01N 30/8693;
(Continued)

(56) References Cited

U.S. PATENT DOCUMENTS

2002/0028005 A1 3/2002 Anderson et al.
2004/0034477 A1 2/2004 McBrien et al.
(Continued)

FOREIGN PATENT DOCUMENTS

JP 2002-214215 7/2002
JP 2007-315941 12/2007
(Continued)

OTHER PUBLICATIONS

Kevin J. Johnson, et al.; "High speed peak machine algorithm of retention time alignment of gas chromatographic data or chemometric analysis", Journal of Chromatography A, 996 (2003) pp. 141 155 (Filed in Parent U.S. Appl. No. 13/806,683).
(Continued)

*Primary Examiner* — Lisa E Peters
(74) *Attorney, Agent, or Firm* — Norris McLaughlin, P.A.

(57) ABSTRACT

Provided are a method of and an apparatus for formulating a multicomponent drug capable of surely making a multicomponent drug meeting criteria for productization with high accuracy into a product. The method and apparatus obtain a chromatogram from an extract or a base of a multicomponent drug, evaluate whether the base meets the criteria for productization based on the obtained chromatogram with high accuracy, and subject the base determined in the high-accuracy evaluating as an accepted one meeting the criteria to dosage form processing, to produce a formulated drug having a given dosage-form. The high-accuracy evaluating is realized by selecting with high accuracy one of reference fingerprints to which peaks of a target fingerprint prepared from the chromatogram are assigned.

12 Claims, 21 Drawing Sheets

(58) Field of Classification Search
CPC .......... G01N 30/8631; G01N 2030/027; G06F 19/707; G06F 19/703; G06F 19/708; G06K 9/00543; A61J 3/02; A61K 45/06
See application file for complete search history.

(56) References Cited

U.S. PATENT DOCUMENTS

| | | |
|---|---|---|
| 2006/0051829 A1 | 3/2006 | Gardner |
| 2007/0181797 A1 | 8/2007 | Uchida et al. |
| 2008/0120041 A1 | 5/2008 | Ridder |
| 2008/0140375 A1 | 6/2008 | Yano |
| 2010/0239172 A1* | 9/2010 | Akiyama |
| 2012/0197541 A1* | 8/2012 | Lewis .................... A61K 31/00 702/22 |

FOREIGN PATENT DOCUMENTS

| | | |
|---|---|---|
| JP | 2008-100918 | 5/2008 |
| JP | 2008-224235 | 9/2008 |
| JP | 2005-351669 | 12/2008 |
| WO | 2009/060975 | 5/2009 |

OTHER PUBLICATIONS

Pharmaceuticals Monthly, vol. 28, No. 3, pp. 67-71, (1986) (Filed in Parent U.S. Appl. No. 13/806,683).
Leach et al., An Introduction to Chemoinformatics, 2007, Springer, Revised Edition, pp. 102-103 (Parent U.S. Appl. No. 13/806,683).
Xie, Chromatographic fingerprint analysis, Journal of Chromatography, 1112 (2006) 171-180 (Parent U.S. Appl. No. 13/806,683).

* cited by examiner

FIG.7

SEVEN

|      | 10.1 | 10.4 | 10.7 | 11.1 | 11.7 | 12.3 | 12.7 | 13.1 | 13.6 | 14.1 | 14.4 |
|------|------|------|------|------|------|------|------|------|------|------|------|
| 10.1 | (0.0)| (0.3)| (0.8)| (1.0)| 1.6  | 2.2  | (2.6)| (3.0)| (3.5)| 4.0  | 4.3  |
| 10.4 |      | 0.0  | 0.3  | 0.7  | 1.3  | 1.9  | 2.3  | 2.7  | 3.2  | 3.7  | 4.0  |
| 10.7 |      |      | 0.0  | 0.4  | 1.0  | 1.6  | 2.0  | 2.4  | 2.9  | 3.4  | 3.7  |
| 11.1 |      |      |      | 0.0  | 0.6  | 1.2  | 1.6  | 2.0  | 2.5  | 3.0  | 3.3  |
| 11.7 |      |      |      |      | 0.0  | 0.6  | 1.0  | 1.4  | 1.9  | 2.4  | 2.7  |
| 12.3 |      |      |      |      |      | 0.0  | 0.4  | 0.8  | 1.3  | 1.8  | 2.1  |
| 12.7 |      |      |      |      |      |      | 0.0  | 0.4  | 0.9  | 1.4  | 1.7  |
| 13.1 |      |      |      |      |      |      |      | 0.0  | 0.5  | 1.0  | 1.3  |
| 13.6 |      |      |      |      |      |      |      |      | 0.0  | 0.5  | 0.8  |
| 14.1 |      |      |      |      |      |      |      |      |      | 0.0  | 0.3  |
| 14.4 |      |      |      |      |      |      |      |      |      |      | 0.0  |

|      | 10.2 | 10.5 | 10.8 | 11.1 | 11.6 | 12.1 | 12.8 | 13.1 | 13.6 | 14.0 |
|------|------|------|------|------|------|------|------|------|------|------|
| 10.2 | (0.0)| (0.3)| (0.6)| (0.9)| 1.4  | 1.9  | (2.6)| (2.9)| (3.4)| 3.8  |
| 10.5 |      | 0.0  | 0.3  | 0.6  | 1.1  | 1.6  | 2.3  | 2.6  | 3.1  | 3.5  |
| 10.8 |      |      | 0.0  | 0.3  | 0.8  | 1.3  | 2.0  | 2.3  | 2.8  | 3.2  |
| 11.1 |      |      |      | 0.0  | 0.5  | 1.0  | 1.7  | 2.0  | 2.5  | 2.9  |
| 11.6 |      |      |      |      | 0.0  | 0.5  | 1.2  | 1.5  | 2.0  | 2.4  |
| 12.1 |      |      |      |      |      | 0.0  | 0.7  | 1.0  | 1.5  | 1.9  |
| 12.8 |      |      |      |      |      |      | 0.0  | 0.3  | 0.8  | 1.2  |
| 13.1 |      |      |      |      |      |      |      | 0.0  | 0.5  | 0.9  |
| 13.6 |      |      |      |      |      |      |      |      | 0.0  | 0.4  |
| 14.0 |      |      |      |      |      |      |      |      |      | 0.0  |

FIG.8

NUMBERS OF MATCHES IN RETENTION TIME APPEARANCE DISTANCE

|  |  | REFERENCE FP RETENTION TIME APPEARANCE PATTERN | | | | | | | | | |
|---|---|---|---|---|---|---|---|---|---|---|---|
|  |  | 1ST ROW | 2ND ROW | 3RD ROW | 4TH ROW | 5TH ROW | 6TH ROW | 7TH ROW | 8TH ROW | 9TH ROW | 10TH ROW |
| TARGET FP RETENTION TIME APPEARANCE PATTERN | 1ST ROW | 7 | 7 | 7 | 8 | 6 | 5 | 4 | 4 | 3 | 2 |
|  | 2ND ROW | 9 | 6 | 6 | 6 | 5 | 2 | 3 | 3 | 2 | 2 |
|  | 3RD ROW | 3 | 8 | 5 | 4 | 5 | 5 | 4 | 2 | 2 | 2 |
|  | 4TH ROW | 6 | 2 | 7 | 6 | 5 | 4 | 4 | 3 | 2 | 1 |
|  | 5TH ROW | 3 | 4 | 5 | 6 | 5 | 4 | 3 | 3 | 2 | 1 |
|  | 6TH ROW | 4 | 3 | 4 | 4 | 5 | 3 | 3 | 2 | 2 | 1 |
|  | 7TH ROW | 2 | 4 | 2 | 2 | 1 | 4 | 3 | 2 | 2 | 2 |
|  | 8TH ROW | 3 | 1 | 3 | 2 | 3 | 3 | 3 | 3 | 3 | 1 |
|  | 9TH ROW | 2 | 2 | 2 | 1 | 1 | 2 | 2 | 2 | 2 | 2 |

FIG.9

DEGREES OF MATCHING IN RETENTION TIME APPEARANCE PATTERN

|  |  | REFERENCE FP RETENTION TIME APPEARANCE PATTERN | | | | | | | | | |
|---|---|---|---|---|---|---|---|---|---|---|---|
|  |  | 1行目 | 2行目 | 3行目 | 4行目 | 5行目 | 6行目 | 7行目 | 8行目 | 9行目 | 10行目 |
| TARGET FP RETENTION TIME APPEARANCE PATTERN | 1行目 | 2.00 | 2.00 | 2.00 | 3.00 | 3.00 | 4.13 | 5.35 | 5.35 | 6.67 | 8.05 |
|  | 2行目 | 0.50 | 3.00 | 3.00 | 3.00 | 4.13 | 8.05 | 6.67 | 6.67 | 8.05 | 8.05 |
|  | 3行目 | 6.67 | 1.15 | 4.13 | 5.35 | 4.13 | 4.13 | 5.35 | 8.05 | 8.05 | 8.05 |
|  | 4行目 | 3.00 | 8.05 | 2.00 | 3.00 | 4.13 | 5.35 | 5.35 | 6.67 | 8.05 | 9.50 |
|  | 5行目 | 6.67 | 5.35 | 4.13 | 3.00 | 4.13 | 5.35 | 6.67 | 6.67 | 8.05 | 9.50 |
|  | 6行目 | 5.35 | 6.67 | 5.35 | 5.35 | 4.13 | 6.67 | 6.67 | 8.05 | 8.05 | 9.50 |
|  | 7行目 | 8.05 | 5.35 | 8.05 | 8.05 | 9.50 | 5.35 | 6.67 | 8.05 | 8.05 | 8.05 |
|  | 8行目 | 6.67 | 9.50 | 6.67 | 8.05 | 6.67 | 6.67 | 6.67 | 6.67 | 6.67 | 9.50 |
|  | 9行目 | 8.05 | 8.05 | 8.05 | 9.50 | 9.50 | 8.05 | 8.05 | 8.05 | 8.05 | 8.05 |

DEGREE OF MATCHING IN RETENTION TIME APPEARANCE PATTERN =
(1 − (NUMBER OF MATCHES IN APPEARANCE DISTANCE/(NUMBER OF PEAKS OF TARGET FP + NUMBER OF PEAKS OF REFERENCE FP − NUMBER OF MATCHES IN APPEARANCE DISTANCE)) × (NUMBER OF PEAKS OF TARGET FP − NUMBER OF MATCHES IN APPEARANCE DISTANCE + 1)

METHOD OF AND APPARATUS FOR FORMULATING MULTICOMPONENT DRUG

REFERENCE TO RELATED APPLICATIONS

The present application is a continuation-in-part application of U.S. patent application Ser. No. 13/806,683, filed Feb. 6, 2013, currently pending, which in turn is the U.S. national stage of PCT/JP2012/003612, filed May 31, 2012. The contents of these applications are incorporated herein by reference in their entirety.

BACKGROUND OF THE INVENTION

1. Field of the Invention

The present invention relates to a method of and an apparatus for formulating a multicomponent drug such as kampo medicine.

2. Description of the Prior Art

As multicomponent materials, for example, there are natural product-originated drugs such as kampo medicines that are drugs (hereinafter, referred to as multicomponent drugs) that are composed of multiple components. The quantitative and qualitative profiles of such drugs change due to a geological factor, an ecological factor, collecting season, a collecting area, a collecting aetas, weather during the growing period, and the like of raw material crude drugs.

Thus, for such multicomponent drugs and the like, predetermined criteria are regulated as qualities for securing the safety and the effectiveness thereof, and national supervising agencies, chemical organizations, manufacturing companies, and the like perform quality evaluations based on the criteria.

Then, a multicomponent drug meeting the criteria for productization is subjected to dosage form processing to produce granules, tablets or the like and thereafter is made into a product through packing.

In general, however, the determination criteria on the quality and the like of a multicomponent drug are set based on the content and the like of one or several distinctive components selected from components in the multicomponent drug.

For example, in 1986, Pharm Tech Japan vol. 28, No. 3, pp 67 to 71, in a case where effective components of a multicomponent drug are not identified, it selects a plurality of components that have physical properties such as a quantitatively analyzability, high water-solubility, a undegradability in hot water, and non-chemical reactability with other components and uses the contents of the components acquired through chemical analysis as evaluation criteria.

In addition, it is well known to apply chromatography to a multicomponent drug, obtain an ultraviolet-visible absorption spectrum for each retention time, and set evaluation criteria based on some pieces of component information included therein.

For example, according to JP 2002-214215 A, some peaks included in HPLC chromatogram data (hereinafter, referred to as a chromatogram) are selected and encoded as barcodes, thereby evaluating a multicomponent drug.

However, in such methods, evaluation targets are limited to "contents of specific components" or "chromatogram peaks of specific components", and thus only some components contained in a multicomponent drug are set as the evaluation targets. Accordingly, since a multicomponent drug includes many components other than components that are evaluation targets, such methods are insufficient as a method of evaluating a multicomponent drug in terms of accuracy.

In order to accurately evaluate the quality of a multicomponent drug, it is necessary to evaluate waveform patterns that cover the all the peak information or almost all peak information with the exclusion of small peaks corresponding to several %. Accordingly, it is necessary to associate all the peaks or almost all peaks with each other between multicomponent drugs.

However, it is difficult to efficiently associate a plurality of peaks with high accuracy. This interferes with an efficient evaluation of multicomponent drugs with high accuracy.

Described more, crude drugs are natural products, and therefore, multicomponent drugs, even which have the same product name, may have slightly different components. Hence, even if drugs have the same quality, content ratios of components thereof may be different from each other or a component present in one drug may not be present in the other drug (hereinafter, referred to as an inter-drug error). In addition, there is also a factor that peak intensity or peak elution time in a chromatogram has no precise reproducibility (hereinafter, referred to as an analysis error). Accordingly, all the peaks of or almost all peaks may not be associated with peaks that are originated from the same components between multicomponent drugs (hereinafter, referred to as peak assignment), thereby interfering with an efficient evaluation with high accuracy.

If quality evaluation of a multicomponent drug can be conducted with high accuracy, it reduces the variation in multicomponent drugs to be subjected to the dosage form processing and the packing. As a result, the high-quality multicomponent drugs can be made into products.

SUMMARY OF THE INVENTION

A problem to be solved is that there is a limit on an efficient evaluation of the quality and the like of multicomponent drugs with high accuracy with use of an existing evaluating method and it is difficult to make multicomponent drugs into products with little variation.

A first aspect of the present invention provides a method of formulating a multicomponent drug capable of surely making a multicomponent drug meeting criteria for productization with high accuracy into a product. The method includes obtaining a chromatogram such as liquid chromatogram (LC), gas chromatogram (GC) from a base of a multicomponent drug, evaluating whether the base meets criteria for productization based on the obtained chromatogram, and subjecting the base determined in the evaluating of the base as an accepted one meeting the criteria for productization to dosage form processing, to produce a formulated drug having a given dosage-form.

Evaluating whether the base meets the criteria includes gathering as a target fingerprint peaks in which each one peak has a height that is a maximum value or an area value in signal strength and retention time points of the peaks detected from the chromatogram, obtaining, as a pattern for each peak of the target fingerprint and a plurality of reference fingerprints corresponding to the target fingerprint and gathering peaks and retention time points of the peaks, appearance distances, height ratios or area ratios between said each peak and subsequent peaks being subsequent to said each peak in the retention time, thereby patterning with a selected scale that is selected from among appearance distance, height ratio and area ratio each peak of the target fingerprint and reference fingerprints that correspond to the target fingerprint and to which peaks and retention time points of the peaks gathered so as to obtain appearance distances, height ratios or area ratios between said each peak and subsequent peaks being subsequent to said each peak in the retention time as a pattern for said each peak, comparing the patterned peaks between the target fingerprint and each one of the reference fingerprints pattern by pattern in a round-robin to find numbers of matches in said any one of appearance distance, height ratio and area ratio as the selected scale, and finding a degree of matching between the target fingerprint and said each one of the reference fingerprints with use of Tanimoto coefficient on the basis of the found numbers of matches to evaluate similarity between the target fingerprint and each one of the reference fingerprints, selecting one of the reference fingerprints based on the similarity, and assigning the peaks of the target fingerprint to peaks of the selected one of the reference fingerprints to evaluate whether the base meets the criteria for productization.

A second aspect of the present invention provides an apparatus for formulating a multicomponent drug. The apparatus includes a chromatographic device obtaining a chromatogram from a base of a multicomponent drug, an evaluating device evaluating whether the base meets criteria for productization based on the obtained chromatogram, and a dosage form processing device subjecting the base determined in the evaluating of the base as an accepted one meeting the criteria for productization to dosage form processing, to produce a formulated drug having a given dosage form.

The evaluating device includes a target fingerprint preparing part gathering as a target fingerprint peaks in which each one peak has a height that is a maximum value or an area value in signal strength and retention time points of the peaks detected from the chromatogram, a patterning part patterning with a selected scale that is selected from among appearance distance, height ratio or area ratio each peak of the target and reference fingerprints that correspond to the target fingerprint and to which peaks and retention time points of the peaks gathered so as to obtain appearance distances, height ratios or area ratios between said each peak and subsequent peaks being subsequent to said each peak in the retention time as a pattern for said each peak according to the selected scale, a matching number extraction part comparing the patterned peaks between the target fingerprint and each one of the reference fingerprints pattern by pattern in a round-robin to find numbers of matches in said any one of appearance distance, height ratio and area ratio as the selected scale, and a matching degree determination part finding a degree of matching between the target fingerprint and said each one of the reference fingerprints with the use of Tanimoto coefficient on the basis of the found numbers of matches to evaluate similarity between the target fingerprint and each one of the reference fingerprints, a selecting part selecting one of the reference fingerprints based on the similarity, and an evaluating part assigning the peaks of the target fingerprint to peaks of the selected one of the reference fingerprints to evaluate whether the base meets the criteria for productization.

The first aspect, for example, when comparing a target fingerprint (hereinafter referred to as target FP) of a multicomponent drug of an evaluation target with reference fingerprints (hereinafter referred to as reference FPs) of evaluation criteria to evaluate the target FP, can simply and quickly select a reference FP suitable for peak assignment of the target FP from among a plurality of reference FPs as a preprocessing of the evaluation.

The first aspect, therefore, performs the peak assignment of the target FP to the selected one of the reference FPs, thereby to improve the accuracy of the peak assignment, the evaluation of the comparison between the target FP and the reference FP, and therefore the evaluation of whether the base of the multicomponent drug meets the criteria for productization.

As a result, the first aspect of the present invention subjects the base of the multicomponent drug determined as an accepted one meeting the criteria for productization with high accuracy to the dosage form processing to make the base into a product. This reduces the variation in multicomponent drugs to be subjected to the dosage form processing and realizes the high quality of the products.

The second aspect operates each part of the evaluating device to simply and quickly select the reference FP suitable for the peak assignment of the target FP. The second aspect, therefore, improves the accuracy of the evaluation of whether the base of the multicomponent drug meets the criteria for productization. This reduces the variation in multicomponent drugs to be subjected to the dosage form processing and realizes the high quality of the products.

BRIEF DESCRIPTION OF THE DRAWINGS

FIGS. 3A to 3C are graphs illustrating FPs of drugs in which FIG. 3A is Drug A, FIG. 3B is Drug B and FIG. 3C is Drug C according to the first embodiment;

FIG. 7 is an explanatory diagram illustrating a number of matches in an appearance distance of the target FP and the reference FP according to the first embodiment;

FIG. 8 is an explanatory diagram illustrating numbers of matches for all the retention time appearance distances of the target FP and the reference FP according to the first embodiment;

FIG. 9 is an explanatory diagram illustrating degrees of matching for all the retention time appearance patterns of the target FP and the reference FP according to the first embodiment;

DETAILED DESCRIPTION OF EMBODIMENTS

A multicomponent drug is defined as a drug that contains a plurality of effective chemical components, and is not limited thereto, but includes a crude drug, a combination of crude drugs, an extract thereof, kampo medicines and the like. In addition, the dosage form is also not particularly limited, and includes, for example, a liquid, an extract, a capsule, a granule, a pill, a suspension emulsion, a powder, a spirit, a tablet, an infusion decoction, a tincture, a troche, aromatic water, a fluid extract and the like, which are prescribed under "General Rules for Preparations" in the Japanese Pharmacopoeia Fifteenth edition. The embodiment exemplifies that granules of a kampo medicine as a formulated-multicomponent drug are produced from a raw material crude drug. The base of the multicomponent drug is an extract or essence extracted from the raw material crude drug in powder form, liquid form or the like. According to the embodiment, the base of the multicomponent drug is a powder extract as explained later.

Specific examples of the kampo medicines are described in Industry Standard and Voluntarily Revision of "Precautions" in 148 Prescriptions for Medical Kampo Drug Formulation and in Guide to General Kampo Prescription (year 1978).

According to the embodiment, it is important to select a reference FP suitable for the peak assignment of the target FP from among a plurality of reference FPs in order to evaluate the multicomponent drug with high accuracy.

Accordingly, the selection of the reference FP, in particular similarity evaluation between the target FP and the reference FP will be explained.

Figure 1:
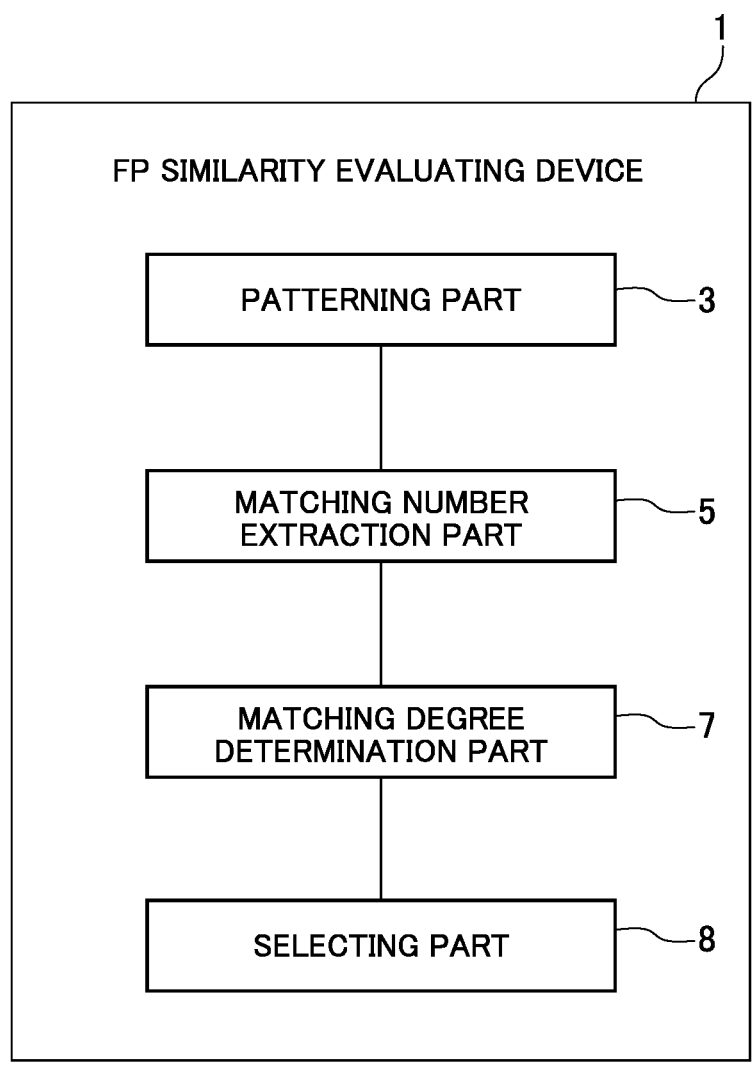
FIG. 1 is a block diagram of a similarity evaluating device for collective data according to a first embodiment.
Figure 2:
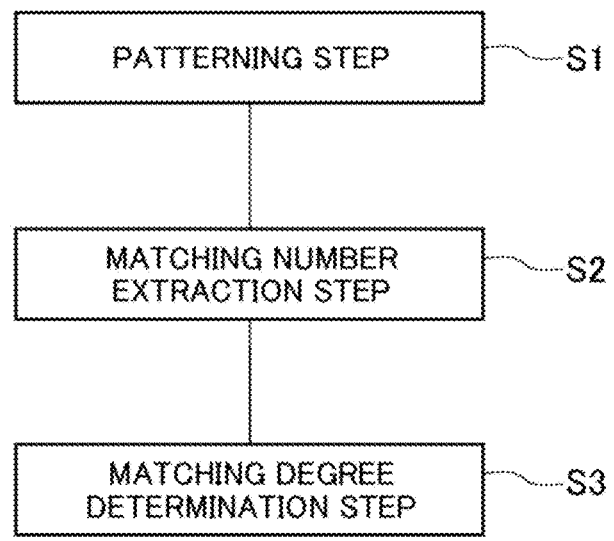
FIG. 2 is a process chart of a similarity evaluating method for collective data according to the first embodiment.

FIG. 1 is a block diagram of the similarity evaluating device for FPs and FIG. 2 is a process chart of the similarity evaluating method for FPs.

As illustrated in FIG. 1 and FIG. 2, the similarity evaluating method of FPs performed by functioning the similarity evaluating device 1 for FPs examines a degree of matching between the target FP and the reference FP.

The similarity evaluating device 1 for FPs is configured by a computer and has CPU, ROM, RAM and the like that are not illustrated. The similarity evaluating device 1 for FPs can implement the similarity evaluating program installed in a computer, to evaluate similarity of the target FP. However, the similarity evaluation for the target FP may be realized by using a similarity evaluating program recording medium that stores the similarity evaluating program thereon by reading out it with the similarity evaluating device 1 for FPs.

The similarity evaluating method for FPs has a patterning step S1 performed by functioning a patterning part 3, a matching number extraction step S2 performed by functioning a matching number extraction part 5, and a matching degree determination step S3 performed by functioning a matching degree determination part 7.

In this similarity evaluating method for FPs, as preprocessing of the final evaluation, a FP of the multicomponent drug suitable for peak assignment of the target FP is selected from among the reference FPs as a plurality of collective data sets. Thus, the similarity evaluating device 1 has a function as a selecting part 8.

In the patterning step S1, each peak of the target FP and the reference FP is patterned with a selected scale by the function of the patterning part 3. This scale according to this embodiment is an inter-retention time distance as the appearance distance of the peaks. Specifically, it will be described below.

In the matching number extraction step S2, each patterned peak is compared in a round-robin, to find numbers of matches between respective patterns by the function of the matching number extraction part 5. These numbers of matches is numbers of matches in the appearance distance in this embodiment. Specifically, it will be described below.

In the matching degree determination step S3, a degree of matching between the respective patterns is found on the basis of the found numbers of matches with use of Tanimoto coefficient by the function of the matching degree determination part 7.

In the matching degree determination step S3, the degree of matching is found using Tanimoto coefficient. Tanimoto coefficient is expressed by $T=c/(a+b-c)$ in which "a" is the number of the peaks of the target fingerprint, "b" is the number of the peaks of the reference fingerprint, and "c" is the number of matches in any one of the appearance distance, height ratio and area ratio. Then, the degree of matching expressed by $D=(1-T)$ and being closer to zero is found.

This degree of matching D may be weighted by d being equal to $(a-c+1)$, which when combined becomes D×d in order to find the degree of matching.

With this weighting, it is possible to select a reference FP having peaks to which the peaks of the target FP matches more at the selecting part 8.

Figure 3:
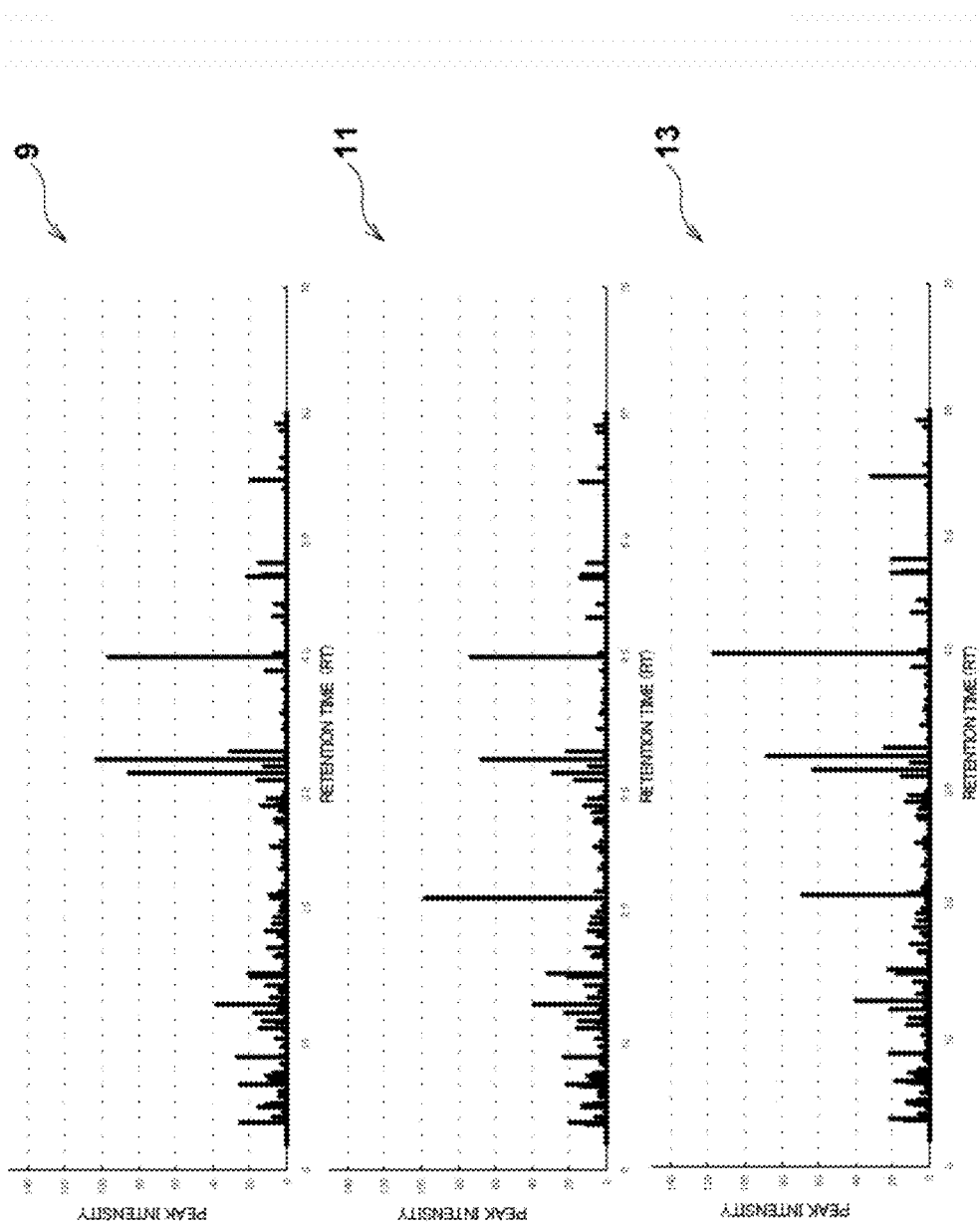

FIG. 3A illustrates a FP of Drug A, FIG. 3B illustrates a FP of Drug B, and FIG. 3C illustrates a FP of Drug C.

For example, if the FP of Drug A is the target FP and the FPs of Drugs B and C are the reference FPs, before each peak of the target FP is assigned to the reference group FPs prepared from Drugs B and C, a reference FP of any one of Drugs B and C suitable for assignment of the target FP is selected from among a plurality of reference FPs, to assign each peak of the target FP to a peak of this selected reference FP.

That is, in order to perform the peak assignment of each peak of the target FP with high accuracy, the degrees of matching between the target FP and the reference FPs in the peak retention time appearance pattern are calculated to select a reference FP having the minimum degree of matching from among all the reference FPs as illustrated in FIG. 4 to FIG. 9.

Figure 4:
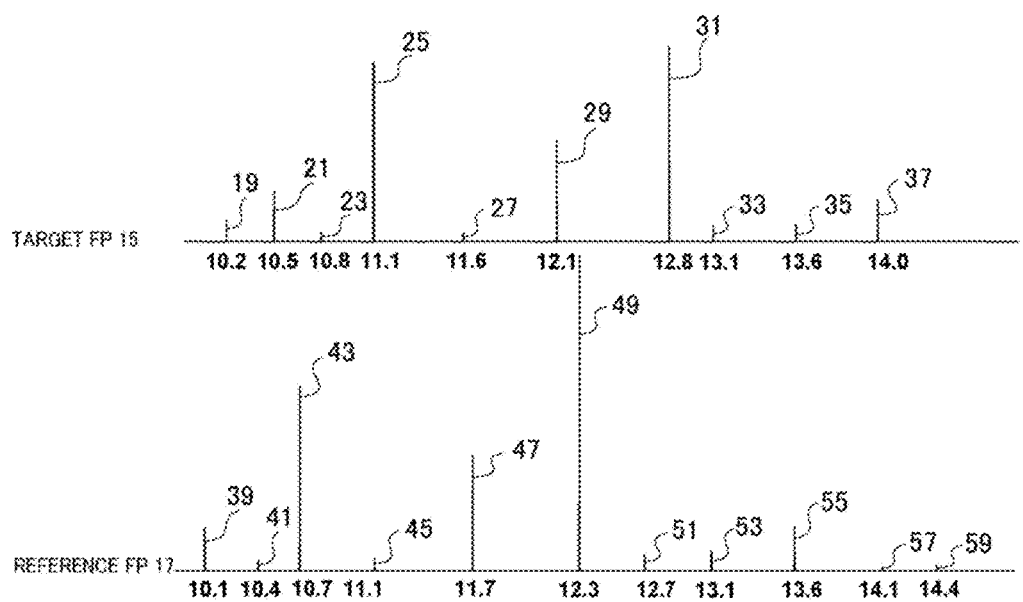
FIG. 4 is an explanatory diagram illustrating retention time points of a target FP and a reference FP according to the first embodiment.
Figure 5:
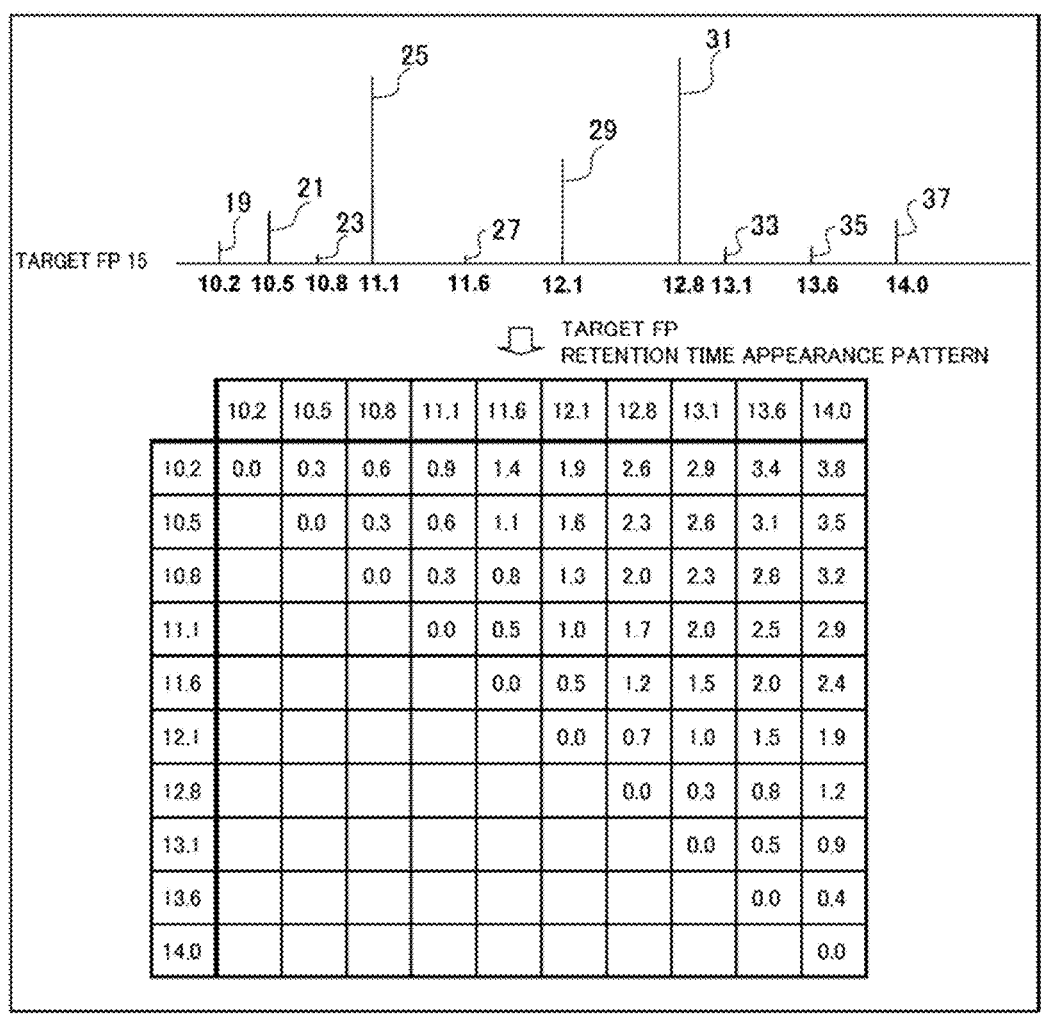
FIG. 5 is an explanatory diagram illustrating a retention time appearance pattern of the target FP according to the first embodiment.
Figure 6:
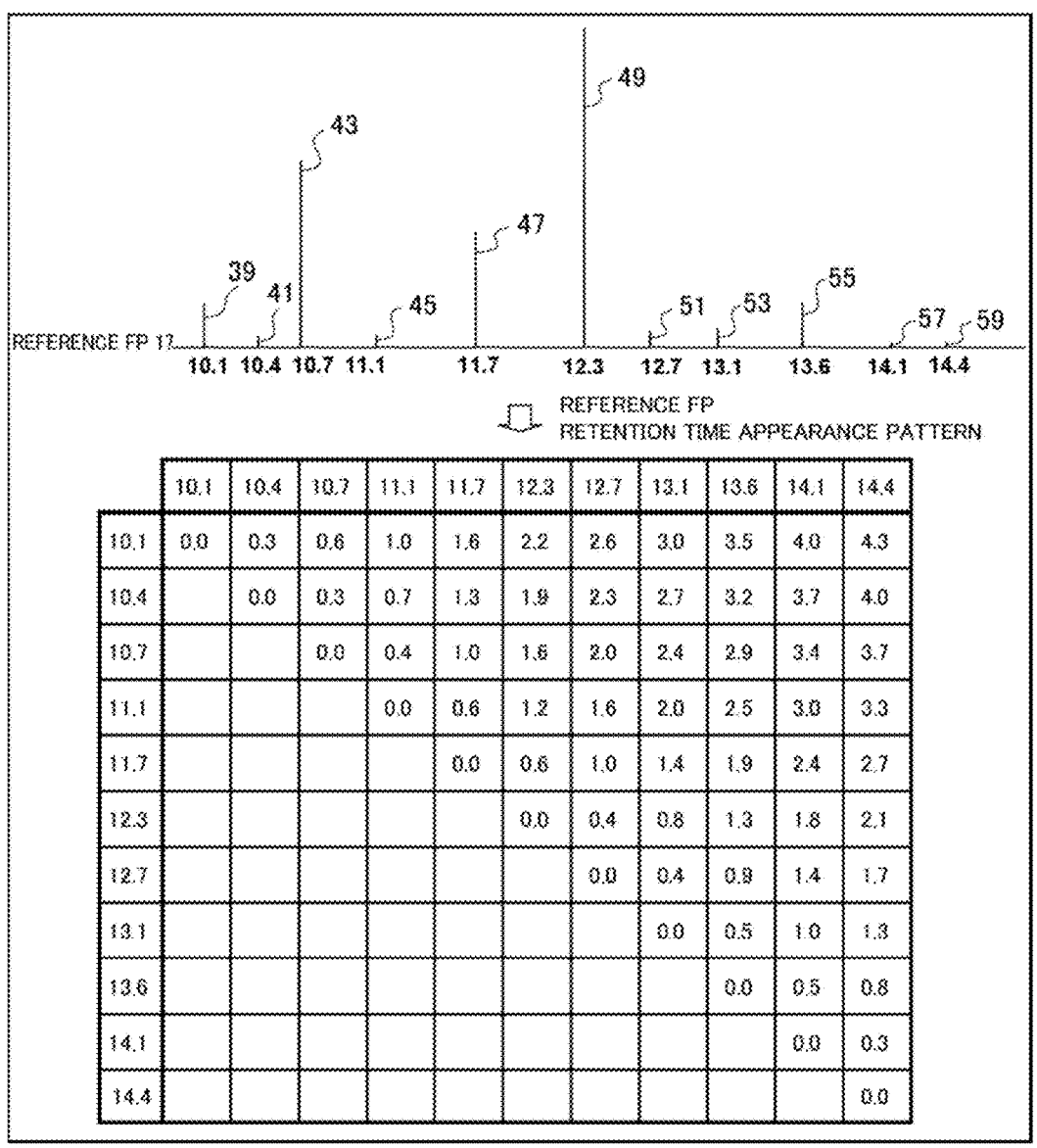
FIG. 6 is an explanatory diagram illustrating a retention time appearance pattern of the reference FP according to the first embodiment.

FIG. 4 to FIG. 9 are diagrams that explain the number of matches in the retention time appearance distance or the degree of matching in the retention time appearance pattern between the target FP and the reference FPs. FIG. 4 is an explanatory diagram illustrating the retention time points of the target FP and the reference FP, FIG. 5 is an explanatory diagram illustrating the retention time appearance pattern of the target FP, and FIG. 6 is an explanatory diagram illustrating the retention time appearance pattern of the reference FP. FIG. 7 is an explanatory diagram illustrating the number of matches in the appearance distance between the target and the reference FPs, FIG. 8 is an explanatory diagram illustrating the number of matches of all the retention time appearance distances of the target FP and the reference FP, and FIG. 9 is an explanatory diagram illustrating the degrees of matching of all the retention time appearance patterns of the target FP and the reference FP.

FIG. 4 shows the retention time point of each of the target FP 15 and the reference FP 17. FIG. 5 and FIG. 6 show the retention time appearance patterns in which calculated are all the inter-retention time point distances from each retention time point of the target FP 15 and the reference FP 17 and are summarized in the form of a table. FIG. 7 shows the number of matches in the retention time appearance distance, which is obtained by comparing the values of the retention time appearance patterns of the target FP and the reference FPs in each cell in each row and by counting and calculating a number of which a difference between the two values is within a predetermined range. FIG. 8 shows the numbers of matches in the retention time appearance distance in the form of a table, which are calculated in all combinations of the target FP and the reference FP. FIG. 9 shows the degree of matching between the retention time appearance patterns in the form of a table, which is calculated based on these numbers of matches.

In the peak assignment process of the target FP 15, each peak of the target FP 15 is assigned to a reference FP that is similar to the target FP 15 in the FP pattern as much as possible. It is an important point to select a reference FP that is similar to this target FP 15 from among a plurality of reference FPs in performing the assignment with high accuracy.

Then, as a method of objectively and simply evaluating similarity with respect to the FP pattern of the target FP 15, the similarity in the FP pattern is evaluated according to the degree of matching in the retention time appearance pattern.

For example, in a case where the retention time points of the target FP 15 and the reference FP 17 are illustrated in FIG. 4, the retention time appearance pattern of each of the target FP 15 and the reference FP 17 are as illustrated in FIG. 5 and FIG. 6, respectively. In FIG. 5 and FIG. 6, the target FP 15 and the reference FP 17 in the upper side are patterned and prepared in the form of a table in which value of each cell is an inter-retention time point distance as illustrated in the lower side.

In FIG. 5, the retention time points of respective peaks (19, 21, 23, 25, 27, 29, 31, 33, 35 and 37) of the target FP 15 are (10.2), (10.5), (10.8), (11.1), (11.6), (12.1), (12.8), (13.1), (13.6) and (14.0).

Accordingly, the inter-retention time point distance between the peak 19 and the peak 21 is (10.5)−(10.2)=(0.3). Similarly, the inter-retention time point distance between the peak 19 and the peak 23 is (0.6), and the inter-retention time point distance between the peak 21 and the peak 23 is (0.3), and the like. The followings are similar, and the target FP appearance pattern are acquired as illustrated in the lower side of FIG. 5.

In FIG. 6, the retention time points of respective peaks (39, 41, 43, 45, 47, 49, 51, 53, 55, 57, and 59) of the reference FP 17 are (10.1), (10.4), (10.7), (11.1), (11.7), (12.3), (12.7), (13.1), (13.6), (14.1) and (14.4).

Accordingly, similarly, the inter-retention time point distances are translated into the reference FP appearance pattern as illustrated in the lower side of FIG. 6.

In this way, the embodiment patterns each one peak of the target FP and the reference FP as well as subsequent peaks with the inter-retention time point distance as a selected scale so that inter-retention time point distances (appearance distances) from a peak to be patterned to respective subsequent peaks are obtained as a pattern for the peak to be patterned.

The peaks patterned in FIG. 5 and FIG. 6 are compared between each one reference FP and the target FP in a round-robin pattern by pattern to find the numbers of matches in inter-retention time point distance as the selected scale. For example, the value of the target FP appearance pattern in each cell of the lower side of FIG. 5 is compared with the value of the reference FP appearance pattern in each cell of the lower side of FIG. 6 so as to compare the corresponding cells to each other in a round-robin in sequence on a per-row basis, for example, the first cell to the first cell, the second cell to the second cell as illustrated in FIG. 7. With this, the numbers of matches are obtained as illustrated in FIG. 8.

In FIG. 7, the patterns according to all the inter-retention time point distance of the retention time appearance patterns of the target FP 15 and the reference FP 17 are compared in a round-robin in sequence on a per-row basis, to calculate the numbers of distances matching within a set range.

For example, when comparing the patterns at the first rows of the target and reference FP retention time appearance patterns of FIG. 7 with each other, circled numerical values match to each other and the number of matches is seven. This matching number of seven is written into a cell for the first rows of the target and reference FP retention time appearance patterns of FIG. 8 as the number of matches in the retention time appearance distance. The same applies to the other rows in FIG. 7, and the 1st to 9th rows of the target FP retention time appearance patterns are compared with the 1st to 10th rows of the reference FP retention time appearance patterns in a round-robin, and the numbers of matches are obtained, respectively.

The results are illustrated in FIG. 8. In FIG. 8, the circled leftmost numerical value of "7" is a result of comparison of the first rows of the respective target and reference FP retention time appearance patterns, and the next numerical value of 7 is a result of comparison of the first row of the target FP retention time appearance pattern with the second row of the reference FP retention time appearance pattern.

In addition, the range of the set value is preferably a range from 0.05 minutes to 0.2 minutes in order to determine the matching of the appearance distances, but is not limited thereto. According to the First embodiment, the set value is 0.1 minutes.

When the degree of matching between the retention time appearance patterns is indicated as RP, the degree of matching ($RP_{fg}$) between a retention time appearance pattern at the f-th row of the target FP 15 and a retention time appearance pattern at the g-th row of the reference FP 17 is calculated with use of Tanimoto coefficient as:

$$RP_{fg} = \{1-(m/(a+b-m))\} \times (a-m+1).$$

In the equation, "a" is the number of the peaks of the target FP 15 (target FP peak number), "b" is the number of the peaks of the reference FP 17 (reference FP peak number), and "m" is the number of matches in the retention time appearance distance (FIG. 8).

The degrees of matching for each retention time appearance pattern (RP) is calculated by the equation based on the numbers of matches in FIG. 8 (FIG. 9).

RP_min is the minimum value of these RPs and is set as the degree of matching between the retention time appearance patterns of the target FP 15 and the reference FP 17. In FIG. 9, (0.50) is the degree of matching between the target FP 15 and the reference FP.

Such degree of matching is calculated for all the reference FPs, the reference FP having the minimum degree of matching is selected, and the peak assignment of the target FP to this reference FP is performed.

Figure 11:
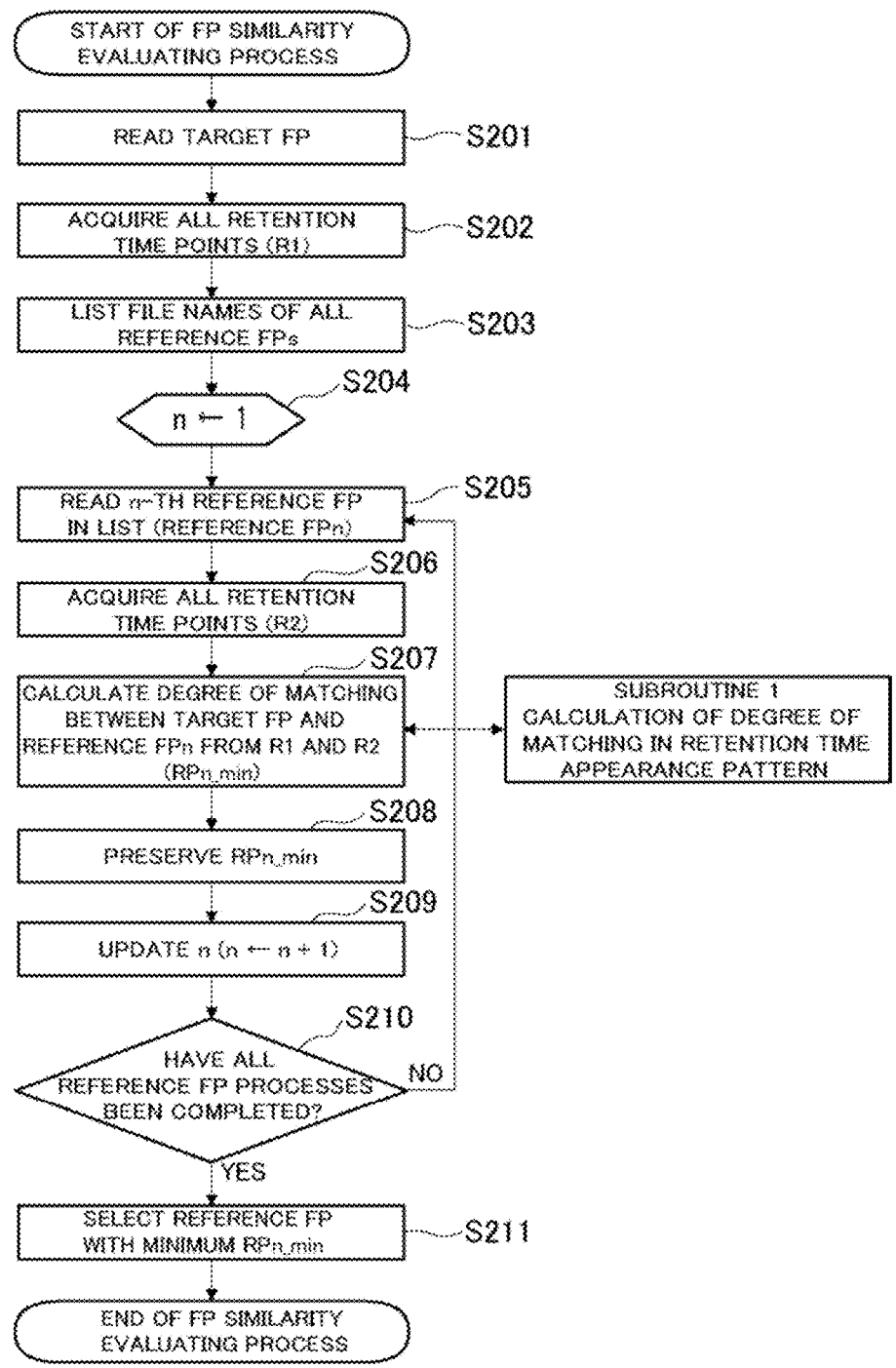
FIG. 11 is a flowchart of data processes in the FP similarity evaluating process according to the first embodiment.
Figure 12:
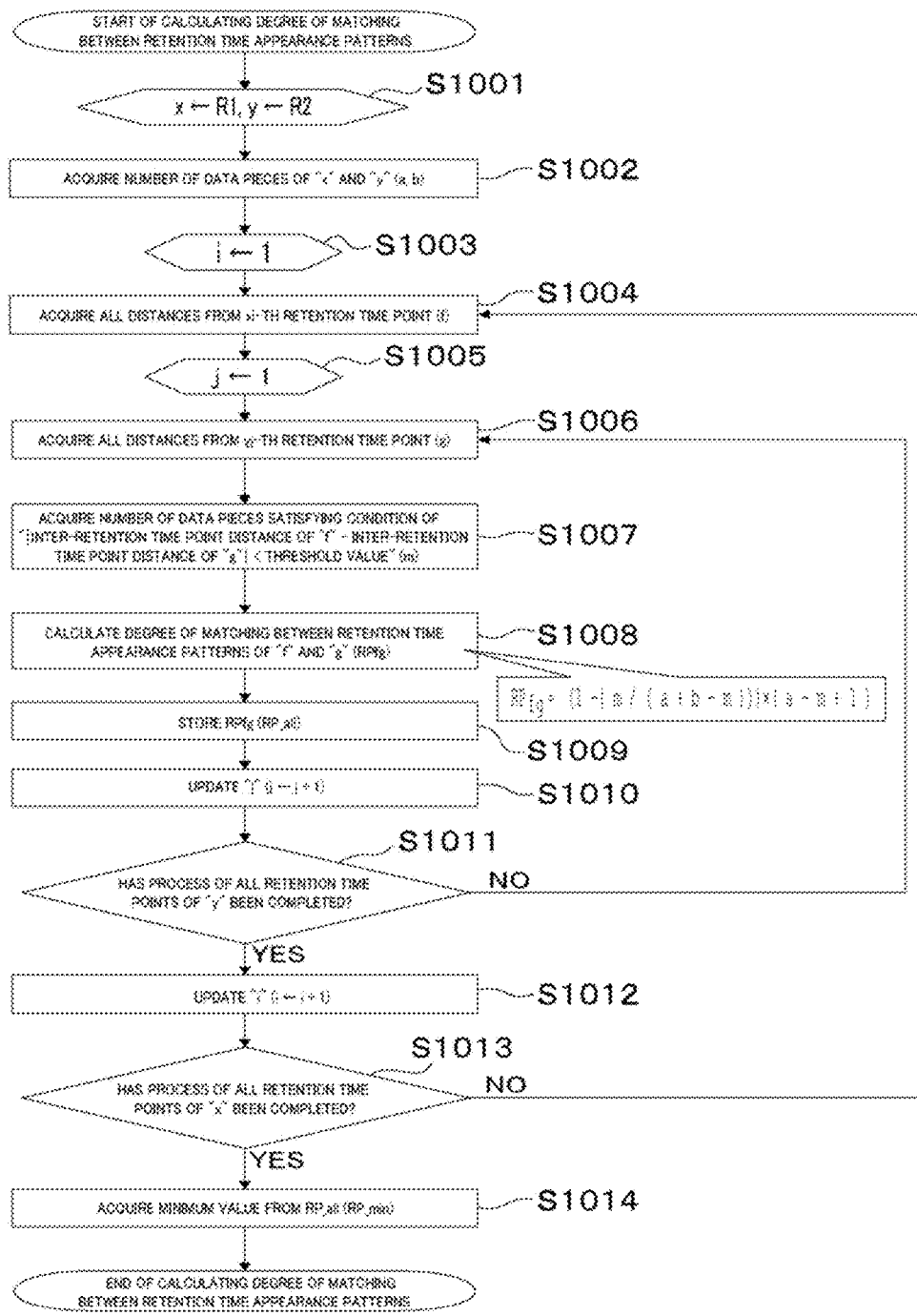
FIG. 12 is a flowchart of calculation process of the degree of matching between the retention time appearance patterns in the FP similarity evaluating process according to the first embodiment.

FIGS. 11 and 12 are flowcharts according to the similarity evaluating program.

FIG. 11 is a flowchart illustrating steps of a whole process for evaluating similarity between FPs, wherein the process starts with a system start-up to cause the computer to execute the patterning function, the matching number extraction function, and the matching degree determination function, thereby evaluating the similarity of the retention time appearance patterns between the target FP 17 and a plurality of reference FPs defined as normal products to select a reference FP suitable for assignment of the target FP 17.

FIG. 12 is a flowchart illustrating details of the "Subroutine 1" in the "FP similarity evaluating process" of FIG. 11. This process calculates the degree of matching between the retention time appearance patterns of FPs (for example, the target FP and the reference FP).

In Step S201, a process of "reading target FP" is executed. This process reads a FP of an assignment target, and the procedure proceeds to Step S202.

In Step S202, a process of "acquiring all retention time points (R1)" is executed. This process acquires all the retention time point information of the target FP read in S201, and the procedure proceeds to Step S203.

In Step S203, a process of "listing file names of all reference FPs" is executed. This process, in order to process all the reference FPs in sequence later, lists file names of all the reference FPs in advance, and the procedure proceeds to Step S204.

In Step S204, as an initial value of a counter for processing the total reference FPs in sequence, "1" is substituted into "n" (n←1), and the procedure proceeds to Step S205.

In Step S205, a process of "reading an n-th reference FP in the list (reference $FP_n$)" is executed. At this process, the n-th FP of the file name list of all the reference FPs listed in S203 is read, and the procedure proceeds to Step S206.

In Step S206, a process of "acquiring all retention time points (R2)" is executed. At this process, all the retention time point information of the reference FP read in S205 is acquired totally, and the procedure proceeds to Step S207.

In Step S207, a process of "calculating the degree of matching between retention time appearance patterns of R1 and R2 ($RP_{n\_}$min)" is executed. At this process, $RP_{n\_}$min is calculated from the retention time points of the target FP acquired in S202 and the retention time points of the reference FP acquired in S206, and the procedure proceeds to Step S208. In addition, detailed calculation flows of $RP_{n\_}$min are explained separately by the subroutine 1 in FIG. 12.

In Step S208, a process of "preserving $RP_{n\_}$min ($RP_{all\_}$min)" is executed. At this process, $RP_{n\_}$min calculated in S207 is preserved in $RP_{all\_}$min, and the procedure proceeds to Step S209.

In Step S209, a process of "updating n (n←n+1)" is executed. At this process, "n+1" is substituted for "n" as the update of "n" to advance the process to the next FP, and the procedure proceeds to Step S210.

In Step S210, a determining process "Have all reference FP processes been completed?" is executed. At this process, it is determined whether all of the reference FPs are processed or not. If processed (YES), the procedure proceeds to Step S211. If there are one or more unprocessed reference FPs (NO), the procedure proceeds to S205 in order to execute the processes of S205 to S210 regarding unprocessed FPs. The processes of S205 to S210 are repeated until the processes of all the reference FPs are completed.

In Step S211, a process of "selecting a reference FP demonstrating the minimum degree of matching from $RP_{all\_}$min" is executed. At this process, $RP_{1\_}$min up to $RP_{n\_}$min calculated for all the reference FPs are compared with each other to select a reference FP demonstrating the minimum degree of matching with respect to the retention time appearance pattern of the target FP.

In Step S1001, a process of "x←R1, y←R2" is executed. At this process, R1 and R2 acquired in S202 and S206 of FIG. 11 are respectively substituted into "x" and "y", and the procedure proceeds to Step S1002.

In Step S1002, a process of "acquiring numbers of data of "x" and "y" (a, b)" is executed. At this process, the numbers of data pieces of "x" and "y" are respectively acquired as "a" and "b", and the procedure proceeds to Step S1003.

In Step S1003, "1" is substituted into "i" (i←1) as the initial value of a counter for sequentially invoking the retention time points of "x", and the procedure proceeds to Step S1004.

In Step S1004, a process of "acquiring all distances from the xi-th retention time point (f)" is performed. In this process, all distances, from the xi-th retention time point, of retention time points after the xi-th retention time point are acquired as "f", and the procedure proceeds to Step S1005.

In Step S1005, "1" is substituted into "j" (j←1) as the initial value of a counter for sequentially invoking the retention time points of "y", and the procedure proceeds to Step S1006.

In Step S1006, a process of "acquiring all distances from the yj-th retention time point (g)" is performed. In this process, all distances, from the yj-th retention time point, of retention time points after the yj-th retention time point are acquired as "g", and the procedure proceeds to Step S1007.

In Step S1007, a process of "acquiring the number of data pieces satisfying a relation of "|inter-retention time point distance of "f"—inter-retention time point distance of "g"|<threshold value" (m)" is performed. In this process, an inter-retention time point distances "f" and "g" acquired in Steps S1004 and S1006 are compared with each other in a round-robin, the number of data pieces satisfying the condition of "|inter-retention time point distance of "f"—inter-retention time point distance of "g"|<threshold value" is acquired as "m", and the procedure proceeds to Step S1008.

In Step S1008, a process of "calculating the degree of matching between the retention time appearance patterns of "f" and "g" ($RP_{fg}$)" is performed. In this process, $RP_{fg}$ is calculated based on "a" and "b" acquired in Step S1002 and "m" acquired in Step S1007 as:

$$RP_{fg}=(1-(m/(a+b-m)))\times(a-m+1).$$

Then, the procedure proceeds to Step S1009.

In Step S1009, a process of "preserving $RP_{fg}$ (RP_all)" is executed. At this process, the degree of matching calculated in S1008 is preserved to RP_all, and the procedure proceeds to Step S1010.

In Step S1010, a process of "updating "j" (j←j+1)" is executed. At this process, "j+1" is substituted into "j" as the update of "j" in order to advance the process of "y" to the next retention time point, and the procedure proceeds to Step S1011.

In Step S1011, a determining process "Has the process been completed at all the retention time points of "y"?" is executed. In this process, it is determined whether or not the process for all the retention time points of "y" has been completed. If completed (YES), it is determined that the process for all the retention time points has been completed to proceed to Step S1012. If not completed (NO), it is determined that one or more retention time points that have not been processed remain in "y", to proceed to Step S1006. In other words, the processes of Steps S1006 to S1011 are repeated until all the retention time points of "y" are processed.

In Step S1012, a process of "updating "i" (i←i+1)" is executed. At this process, "i+1" is substituted into "i" as the update of "i" in order to advance the process of "x" to the next retention time point, and the procedure proceeds to Step S1013.

In Step S1013, a determining process "Has the process been completed at all the retention time points of "x"?" is executed. In this process, it is determined whether or not the process for all the retention time points of "x" has been completed. If completed (YES), it is determined that the process for all the retention time points of "x" has been completed to proceed to Step S1014. If not completed (NO), it is determined that one or more retention time points that have not been processed remain in "x", to proceed to Step S1004. In other words, the processes of Steps S1004 to S1013 are repeated until all the retention time points of "x" are processed.

In Step S1014, a process of "acquiring a minimum value from RP_all (RP_min)" is performed. In this process, the minimum value in RP_all in which RPs for all the combinations of the retention time appearance patterns of the target FP and the reference FP are stored is acquired as RP_min, and RP_min is input to Step S207 of FIG. 11 to finish the process of calculating the degree of matching between the retention time appearance patterns.

With the aforementioned similarity evaluation, the embodiment selects the reference FP suitable for the peak assignment of the target FP from among the reference FPs and therefore allows the subsequent evaluation of the target FP based on the peak assignment to the reference FP to be performed with high accuracy.

Figure 13:
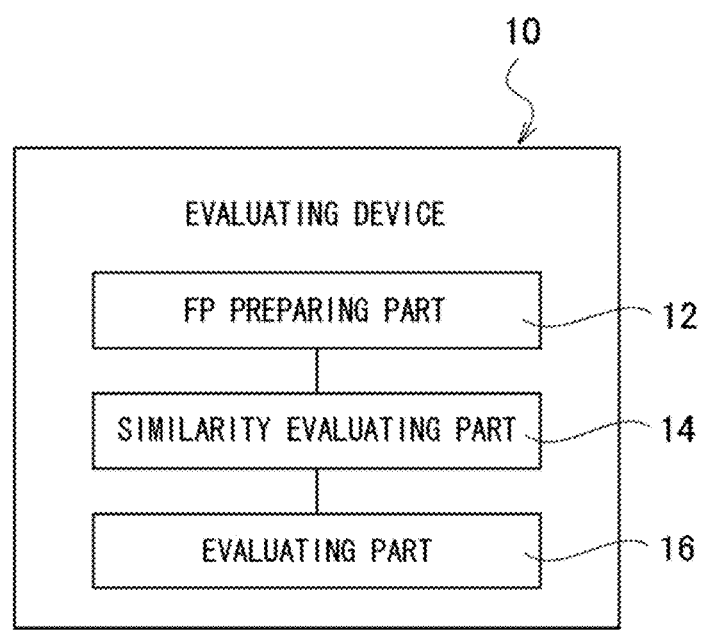
FIG. 13 is a block diagram illustrating an evaluating device to which the similarity evaluating device is applied according to the first embodiment.

FIG. 13 is a block diagram illustrating an evaluating device 10 to which the similarity evaluating device 1 is applied.

The evaluating device 10 has functions as a FP preparing part 12 and an evaluating part 16 as well as a similarity evaluating part 14 serving as the similarity evaluating device 1. With this, the evaluating device 10 prepares a target FP from a 3D chromatogram of a multicomponent drug, selects a reference FP most suitable for peak assignment of the prepared target FP, and evaluates or determines whether an extract of the multicomponent drug meets the criteria for productization through similarity evaluation based on the peak assignment of the target FP to the selected reference FP.

The FP preparing part 12 gathers as a target FP peaks in which each one peak has a height that is a maximum value or an area value in signal strength and retention time points of the peaks detected from a 3D chromatogram of a multicomponent drug. According to the embodiment, the height of the peak is the maximum value in signal strength.

Figure 14:
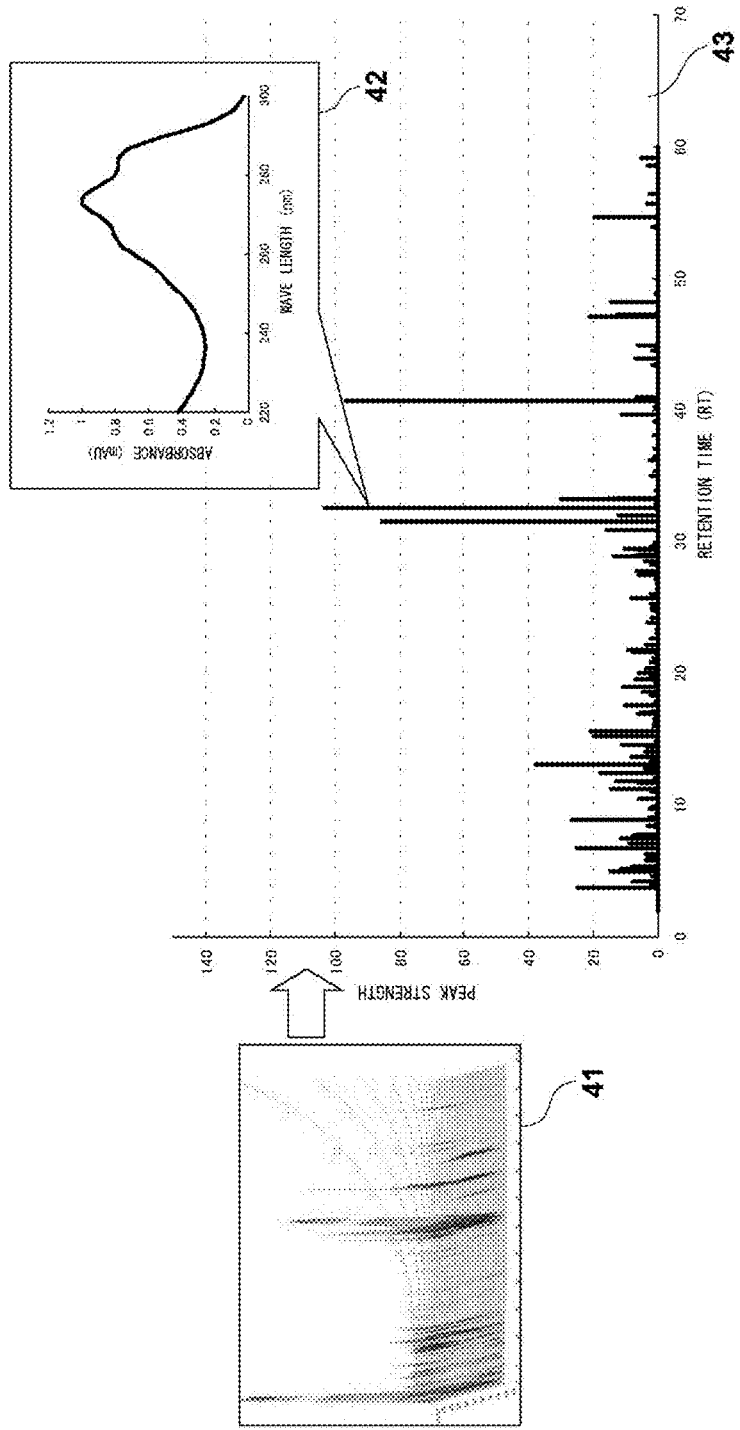
FIG. 14 is an explanatory view illustrating the target FP according to the first embodiment.

FIG. 14 is an explanatory view illustrating the target FP.

The FP preparing part 12, for example, as illustrated in FIG. 14, is a functional part that prepares a target FP 43 (hereinafter, it may be simply referred to as an "FP 43") by extracting a plurality of peaks at a specific detection wavelength, retention time points thereof, and UV spectra from a 3D chromatogram 41 as a chromatogram of a kampo medicine. The FP 43 corresponds to the target FP 9 in FIG. 3A and the target FP 15 in FIG. 4.

The FP 43, similarly to the 3D chromatogram 41, is configured by three-dimensional information (peaks, retention time points, and UV spectra).

The FP 43, therefore, is data that directly succeed to information unique to the drug. In spite of that, the data volume is compressed at the ratio of about 1/70, and therefore, the amount of information to be processed is much smaller than that of the 3D chromatogram 41, thereby increasing processing speed.

Figure 18:
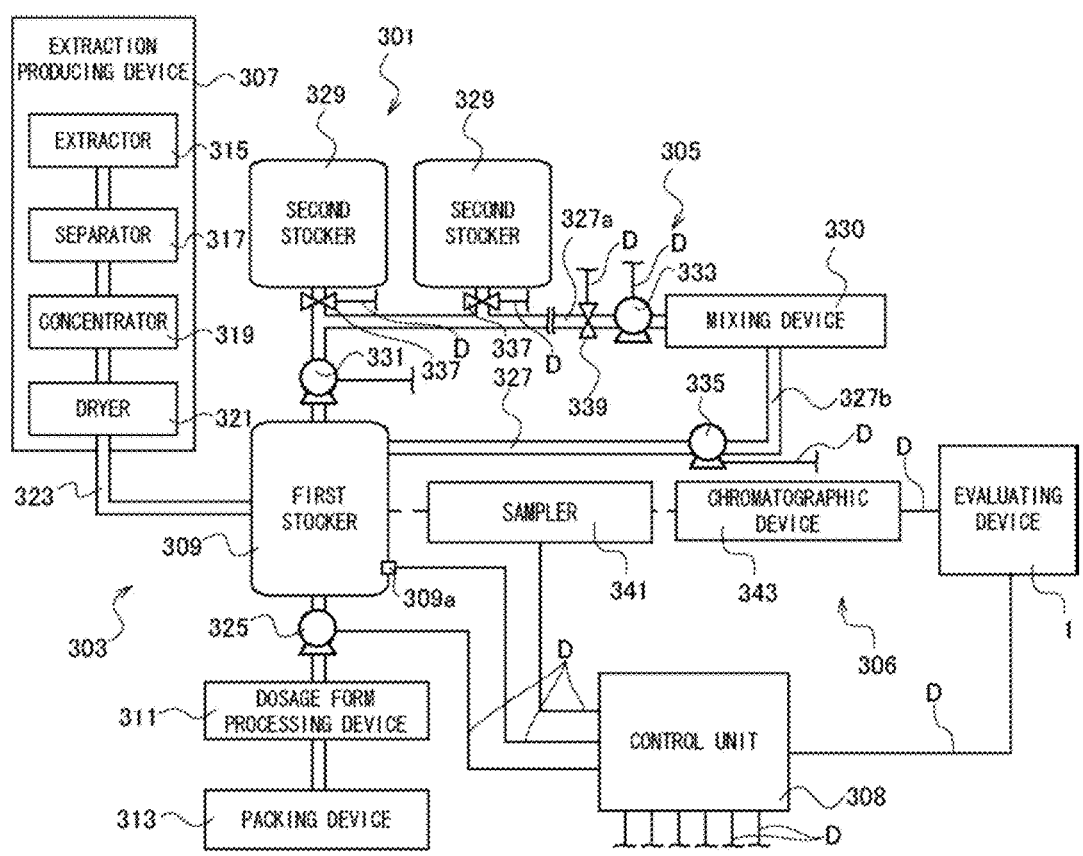
FIG. 18 is a schematic block diagram illustrating a formulating apparatus to which the evaluating device is applied according to the first embodiment.

The 3D chromatogram 41 is a result of applying high performance liquid chromatography (HPLC) to a powder extract of a kampo medicine 39 as the multicomponent drug in the chromatographic device 343 (FIG. 18). In the 3D chromatogram 41, a movement speed of each component appears to represent as a movement distance during specific time, or an appearance in a time series from a column end is represented in a chart. In the HPLC, detector responses are plotted with respect to the time axis, and appearance time points of peaks are called retention time points.

Although the detector is not particularly limited, an absorbance detector employing an optical characteristic is used as the detector. A peak is three-dimensionally acquired as a signal strength according to a detection wavelength of ultraviolet (UV). As a detector employing an optical characteristic, a transmittance detector may be used.

The detection wavelengths are not particularly limited, and are a plurality of wavelengths selected preferably from a range of 150 nm to 900 nm, selected more preferably from a range of 200 nm to 400 nm corresponding to a UV-visible absorption range, and selected further more preferably from a range of 200 nm to 300 nm.

The 3D chromatogram 41 at least includes a number (lot number), retention time points, detection wavelengths, and peaks of a kampo medicine as data.

In the 3D chromatogram 41, as illustrated in FIG. 14, the x-axis represents the retention time point, the y-axis represents the detection wavelength, and the z-axis represents signal strength.

The FP 43 at least includes as data a number (lot number), retention time points, peaks at a specific wavelength, and UV spectra of the kampo medicine.

The FP 43 is two-dimensionally represented with the x-axis representing the retention time points and the y-axis representing the peaks for the specific detection wavelength. However, the FP 43 is data that includes UV spectrum information for each peak that is similar to the UV spectrum 42 represented with respect to one peak (FIG. 14).

Namely, the FP 43 is configured by the combination of the two-dimensional information, and therefore indicates the magnitudes (heights) and the retention time points of the peaks in two dimension and has a two-dimensional UV spectrum assigned at each one peak.

The specific detection wavelength for which the FP 43 is prepared is not particularly limited and may be selected in various manners. However, it is important for the FP 43 to include all the peaks of the 3D chromatogram in order to succeed to the information. Accordingly, in Embodiment 1, the detection wavelength is set to 203 nm that includes all the peaks of the 3D chromatogram.

Meanwhile, there are cases where all the peaks are not included for a single wavelength. In such a case, a plurality of detection wavelengths are set to prepare a FP that includes all the peaks by combining the plurality of wavelengths as explained later.

In the first embodiment, although the peak is set as the maximum value of the signal strength (peak height), the area value may be used as the peak. In addition, a FP may not include UV spectra, so that the FP is set as two-dimensional display information in which the x-axis represents the retention time points and the y-axis represents the peaks for a specific detection wavelength. In such a case, the FP can be prepared from a 2D chromatogram as a chromatogram that includes a number (lot number) and retention time points of a kampo medicine as data.

Figure 15:
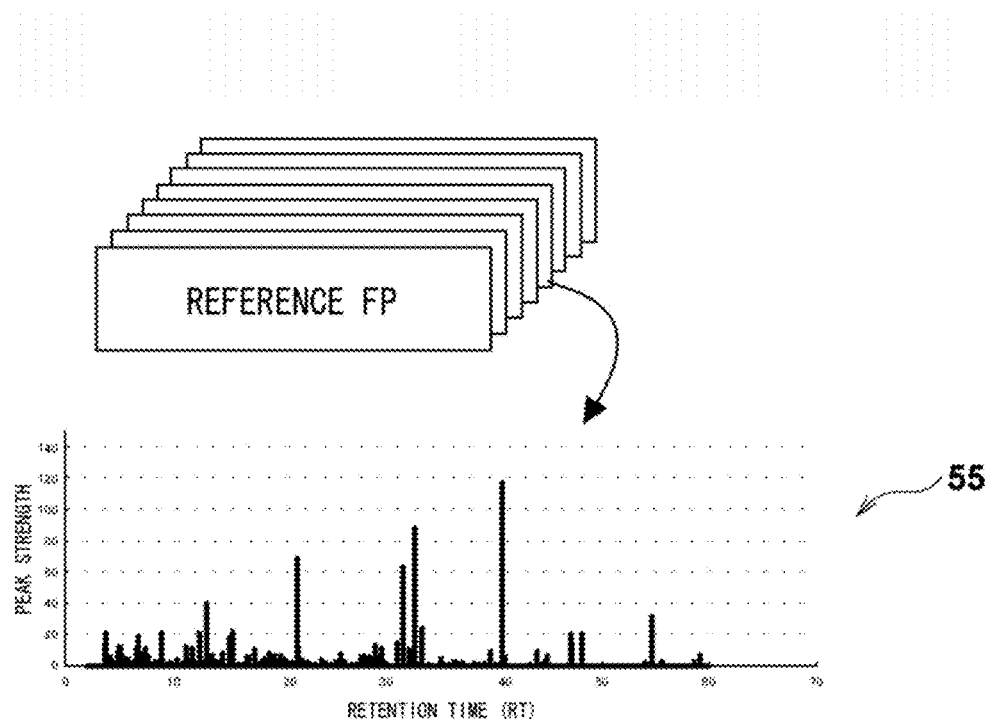
FIG. 15 is an explanatory view illustrating selected one of reference FPs according to the first embodiment.

For the target FP 43 prepared at the FP preparing part 12 of FIG. 13, the similarity evaluating part 14 selects a reference FP most suitable for peak assignment from among reference FPs in the same way as the similarity evaluating device 1. FIG. 15 indicates the selected reference FP.

The evaluating part 16 assigns the peaks of the target FP 43 to the peaks of the selected reference FP 55 to evaluate similarity between the target FP 43 and the reference FP 55 and evaluates whether the extract of the multicomponent drug meets the criteria for productization.

In the peak assignment, corresponding peaks are specified between the target FP 43 and the reference FP 55. A method of specifying the corresponding peaks can be selected from among various methods. For example, the corresponding peaks are specified by comparison in peak size, retention time, UV spectrum, information of peripheral peaks or appropriate combination of them.

The evaluating part 16 according to the embodiment assigns the peaks of the target FP 43 to respective peaks of a reference group FP 18 based on the peak assignment of the target FP to the reference FP 55.

Figure 16:
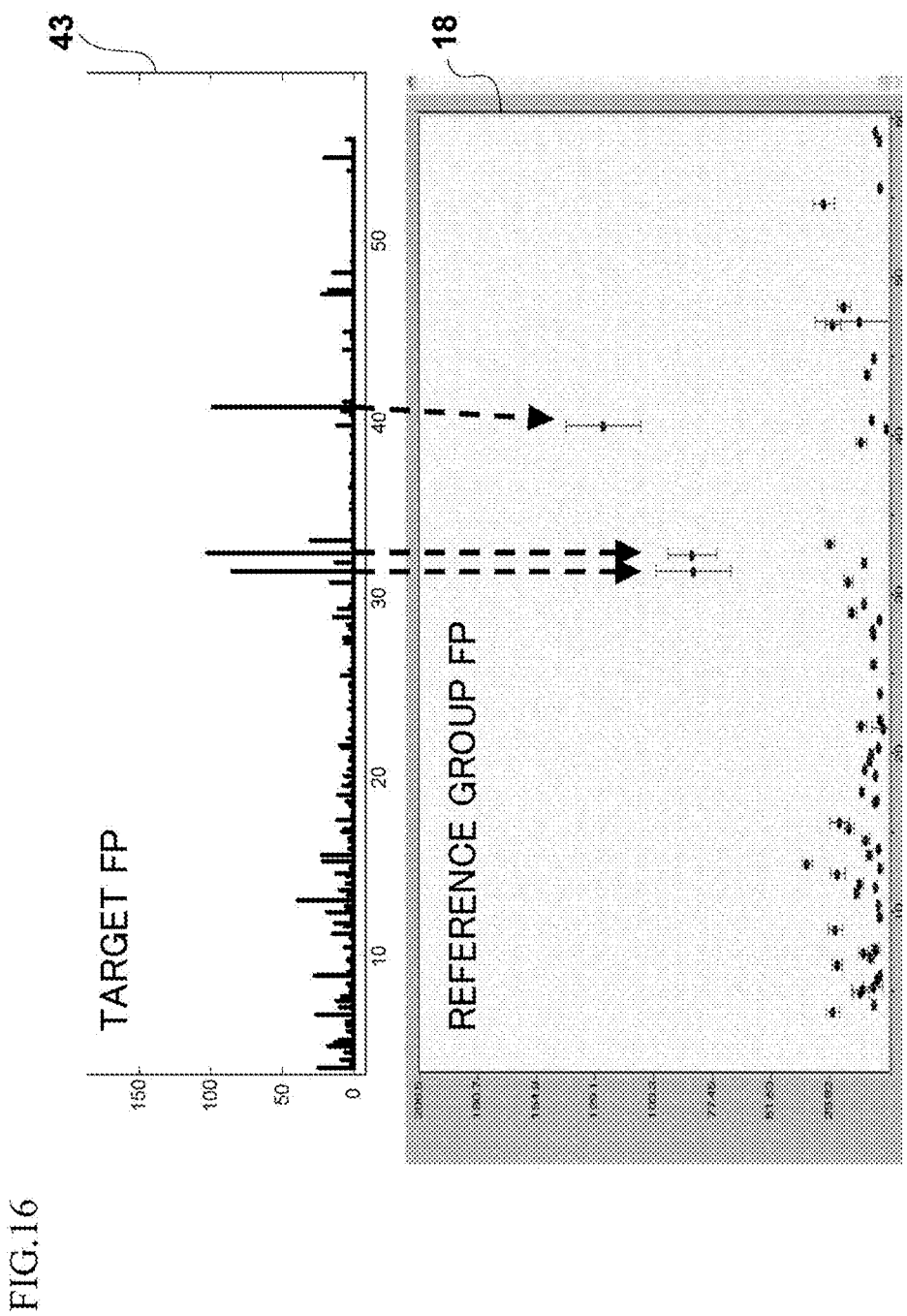
FIG. 16 is an explanatory view illustrating peak assignment of the target FP to a reference group FP according to the first embodiment.
Figure 17:
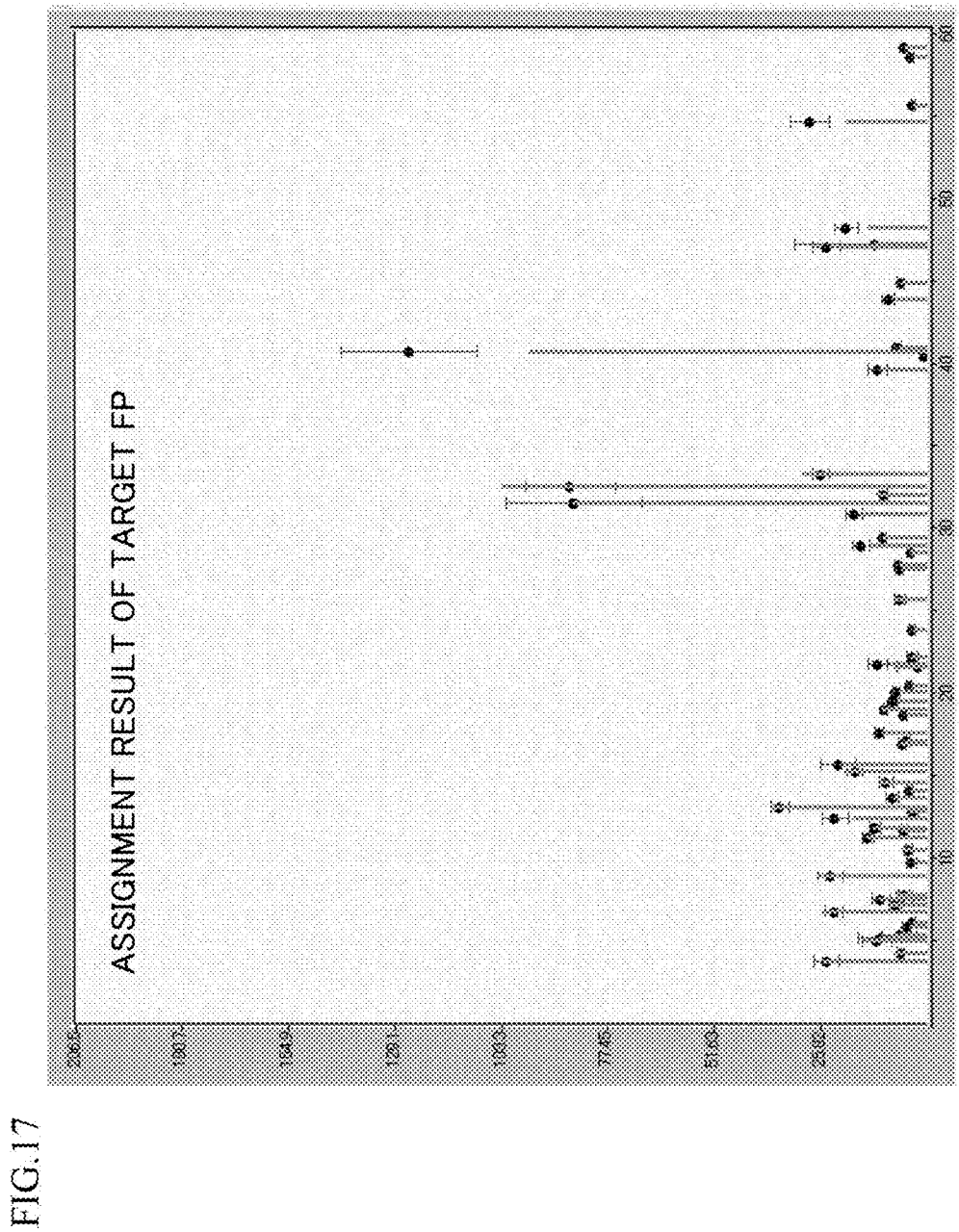
FIG. 17 is a diagram illustrating a state of the peak assignment of FIG. 16.

FIG. 16 is an explanatory view illustrating the peak assignment of the target FP 43 to the reference group FP 18 and FIG. 17 is a diagram illustrating a state of the peak assignment.

In FIGS. 16 and 17, the reference group FP 18 is prepared by performing an assignment process like the above for all the plurality of reference FPs determined as normal products, and each peak is represented by an average value (black point) of assigned peaks±standard deviation (vertical line).

Based on the assignment of the target FP 43 to the reference group FP 18, the evaluating part 16 compares and evaluates the peaks of the target FP 43 and the peaks of the plurality of reference FPs. In the embodiment, the evaluating part 16 evaluates equivalency between the target FP 43 and the reference group FP 18 with Mahalanobis-Taguchi method (hereinafter referred to as MT method).

MT method represents a calculation technique that is generally known in quality engineering. For example, MT method is described in pp 136 to 138, "Mathematics for Quality Engineering" published by Japanese Standards Association (2000); in pp 454 to 456 of Quality Engineering of Application Course "Technical Developments in Chemistry, Pharmacy and Biology" published by Japanese Standards Association (1999); in pp 78 to 84 of Quality Engineering 11(5) (2003); and in "Introduction to MT System" (2008).

In addition, MT method program software that is commercially available in the market can be used. As such commercially-available MT method program software, there are "ATMTS" provided by Angle Try Associates, "TM-ANOVA" provided by Japanese Standards Association, an "MT method for Windows" provided by OHKEN Co., Ltd, and the like.

The evaluating part 16 assigns a variable axis according to MT method to one of the lot number and the retention time point of a kampo medicine or the UV detection wavelength of the target FP 43 and sets the peaks as feature values according to MT method.

Although the assignment of the variable axis is not particularly limited, it is preferable that the retention time point is assigned to a so-called category axis according to MT method, the number of a multicomponent-based drug is assigned to a so-called number row axis, and the peak is assigned to a so-called feature value according to MT method.

Here, the category axis and the number row axis are defined as below. According to MT method, an average value $m_j$ and a standard deviation $\sigma_j$ are acquired for a data set $X_{ij}$, a correlation coefficient "r" between "i" and "j" is acquired from a value $x_{ij}=(X_{ij}-m_j)/\sigma_j$ that is the standardized $X_{ij}$, and accordingly, a unit space or a Mahalanobis distance is acquired. At this time, the category axis and the number row axis are defined such that "the average value $m_j$ and the standard deviation $\sigma_j$ are acquired for each value of the category axis by changing the value of the number row axis."

Based on the data and the feature values to which the axes are assigned, a reference point and an unit quantity (it may be abbreviated as a "unit space") are acquired using MT method. Here, the reference point, the unit quantity, and the unit space are defined in accordance with the description of MT method presented in the above-described literatures.

According to MT method, a Mahalanobis distance (hereinafter referred to as MD value) is acquired as a value that represents the degree of a difference between a drug to be evaluated and the unit space. The MD value is defined in the same way as the description of MT method presented in the literatures, and the MD value is acquired with the method described in the literatures.

By using the MD value acquired in this manner, the drug to be evaluated can be evaluated by determining the degree of a difference from a plurality of drugs defined as normal products.

For example, by performing the assignment process for a target FP, a MD value (MD value: 0.25, 2.99, or the like) can be acquired in accordance with MT method.

When this MD value is evaluated with respect to an MD value of a normal product, MD values are similarly acquired for a plurality of drugs defined as normal products. A threshold value is set from the MD values of these normal products. The MD value of the evaluation target drug is plotted as an evaluation result of the evaluating part 16 to determine whether a normal product or an abnormal product. In the evaluation result of the evaluating part 16, for example, an MD value of 10 or less is determined as a normal product.

In addition, it is sufficient for the evaluating part 16 to be able to compare and evaluate the equivalency between the target FP 43 and the reference group FP 18, and therefore, a pattern recognition technique other than MT method or the like can be used.

The evaluating device 10 is installed into a formulating apparatus to evaluate an extract or essence of a multicomponent drug extracted from a raw material crude drug and allow an extract highly meeting the criteria for productization to be made into a product.

FIG. 18 is a schematic block diagram illustrating the formulating apparatus 301.

As illustrated in FIG. 18, the formulating apparatus 301 has a formulating line 303, a mixing line 305, and an evaluating line 306, and a control unit 308.

The formulating line 303 includes a first pipeline 323 serving as a first conveyor, an extract producing device 307 serving as a base producing device, a first stocker 309, a dosage form processing device 311, and a packing device 313. With this, the formulating line 303 is configured to extract an essence as the base of the multicomponent drug from the raw material crude drug, subject the extracted essence or extract of the multicomponent drug meeting criteria for productization to dosage form processing to produce a formulated drug and thereafter pack the formulated drug. The evaluation of whether the extract meets the criteria is conducted at the evaluating line 306 as explained later.

The first pipeline 323 is led from the extract producing device 307 to the packing device 313 through the first stocker 309 and the dosage form processing device 311, convey an extract produced by the extract producing device 307.

The extract producing device 307 is composed of an extractor 315, a separator 317, a concentrator 319 and a dryer 321 that are connected to each other through the first pipeline 323. The configuration of the extract producing device 307 is an example and therefore may exclude the dryer 321, for example. The excluded dryer may be laid downstream of the first stocker 309. The embodiment produces the extract with the extract producing device 307. The extract producing device 307 and the production of the extract, however, may be omitted.

The extractor 315 receives the raw material crude drug therein and extracts an essence as a liquid extract using a solvent. The extractor 315 is realized by, for example, a multipurpose extractor "TEX2015" manufactured by IZUMI FOOD MACHINERY Co., Ltd., a rotocel extractor manufactured by Mitsubishi Kakoki Kaisha, Ltd., a centrifugal extractor "Ultrex" manufactured by Hitachi, Ltd., or the like.

The raw material crude drug in this embodiment is cut and compounded in advance. The raw material crude drug, however, may be an uncut one. As the solvent, water, ethanol, acetic acid and the like are exemplified for hot and cold extraction. In a case of the kampo medicine according to the embodiment, it is preferred that the hot extraction is conducted at temperature of 90-100° C. using water as the solvent. The liquid extract, i.e., extraction liquid produced at the extractor 315 is conveyed to the separator 317 through the first pipeline 323.

The separator 317 removes impurities from the extraction liquid through solid-liquid separation. The separator 317 is realized by, for example, a basket type centrifugal separator "TEC-48" or decanter type centrifugal separator manufactured by TANABE WILLTEC INC., the centrifugal extractor "Ultrex" manufactured by Hitachi, Ltd., or the like. From the separator 317, the extraction liquid is conveyed to the concentrator 319 through the first pipeline 323.

The concentrator 319 concentrates or condenses the extraction liquid and is realized by, for example, flash method concentration equipment "REV-100/90" or global concentration equipment manufactured by HISAKA WORKS, LTD., a centrifugal thin film concentrator or centritherm evaporator Alfa Laval Ltd., or the like. As the concentration method for the extraction liquid, vacuum concentration is used in general. As the condition of the vacuum concentration for the kampo medicine, the degree of vacuum is set in a range of 30-760 mmHg, the evaporating temperature is set equal to or less than 100° C., preferably in a range of 30-50° C., and the like, for example. The concentrated extraction liquid, i.e., concentrated liquid is conveyed from the concentrator 319 to the dryer 321 through the first pipeline 323.

The dryer 321 dries the concentrated liquid to convert the same into powder. The dryer 321 is realized by, for example, a vacuum belt dryer (SBD) manufactured by HISAKA WORKS, LTD., a spray dryer "OC-20" manufactured by OKAWARA MFGCO., LTD., a spray dryer for producing medicines manufactured by GEA Process Engineering Inc., or the like.

The drying method employs but is not limited to a spray drying method, a vacuum drying method or a freeze drying method depending on a kind of dryer 321. For example, the spray drying method sprays with an atomizer the concentrated liquid into a thermal current within a drying chamber maintained at high temperature of 60-300° C. so that the solvent instantly evaporates to dry the concentrated liquid. The vacuum drying method dries, under the condition in which the degree of vacuum is equal to or less than the 760 mmHg and the temperature is in a range of 5-100° C., the concentrated liquid that is the extraction liquid sufficiently subjected to the vacuum concentration. The freeze drying method freezes the concentrated liquid at the temperature of −80-0° C. and then dries the same by directly sublimating the solvent in a vacuum state being equal to or less than 1 mmHg. The powder extract due to such drying is conveyed to the first stocker 309 through the first pipeline 323.

The first stocker 309 is arranged or laid downstream of the extract producing device 307 on the first pipeline 323 to accommodate the powder extract produced at the extract producing device 307. In particular, the first stocker 309 tentatively stores the powder extract during the evaluating line 306 evaluates the powder extract.

The first stocker 309 is realized by, for example, a general tank or the like. On the downstream side of the first stocker 309, the first pipeline 323 has a blower 325. With the blower 325, the powder extract is conveyed from the first stocker 309 to the dosage form processing device 311.

The dosage form processing device 311 subjects the powder extract of the multicomponent drug to the dosage form processing to make the same into a formulated drug having a given dosage form. For example, the dosage form processing device 311 produces granules or tablets according to an intended dosage form.

According to the embodiment, the dosage form processing device 311 is configured to produce the granules and realized by, for example, a horizontal extrusion granulator "Granumaster" manufactured by OKAWARA MFGCO., LTD., a multistage roll granulator manufactured by Kurimoto, Ltd., or the like. In the case of producing tablets, the dosage form processing device 311 may be realized by, for example, a tableting machine "AQUARIUS G" manufactured by KIKUSUI SEISAKUSHO LTD., "αX-MS type" medium-sized tableting machine manufactured by HATA TEKKOSHO CO., LTD., or the like.

The granules produced at the dosage form processing device 311 are conveyed to the packing device 313 through the first pipeline 323.

The packing device 313 subdivides and packs the granules or tablets to complete productization. The packing device 313 for the granules is realized by, for example, a powder and granule packing machine "MS101" manufactured by SANKO MACHINERY CO., LTD. or the like. In the case of the tablets, the packing device 313 is realized by, for example, a tablet four side sealing machine manufacture by ASAHI SHIKO Corporation or the like.

The mixing line 305 includes a second pipeline 327, a plurality of second stockers 329, and a mixing device 330. With this, the mixing line 305 is configured to obtain a powder extract that does not meet the criteria for productization from the first stocker 309 and store the same, mix two or more stored powder extracts and return the mixed powder extracts to the first stocker 309. In FIG. 18, two second stockers 329 are indicated, however, the number of the second stockers 329 is not limited thereto.

The second pipeline 327 is led from and back to the first stocker 309 so as to make a loop. The second pipeline 327 includes a taking-out line 327a led out from the first stocker 309 and a return line 327b returning back to the first stocker 309.

The taking-out line 327a has a blower 331 for storing a powder extract and a blower 333 for mixing powder extracts. The return line 327b has a blower 335 for returning a powder extract.

Further, the second pipeline 327 has valves 337 and 339 laid upstream of the second stockers 329 and the mixing device 330 for storing a powder extract and mixing powder extracts, respectively.

The taking-out line 327a is configured to selectively convey a powder extract to one of the second stockers 329 according to control of the blower 331 and the valves 337. Further, the taking-out line 327a is configured to selectively take out stored powder extracts from the second stockers 329 and convey the same to the mixing device 330 according to control of the blower 333 and the valves 337 and 339. The return line 327b is configured to convey a mixed extract as a mixed base from the mixing device 330 to the first stocker 309 according to control of the blower 335.

In this specification, the powder extract means the individual powder extract produced by the extract producing device 307 and the mixed extract means a mixture of the individual powder extracts.

The second stockers 329 are laid on the second pipeline 327, in particular the taking-out line 327a to store a powder extract that does not meet the criteria for productization and is conveyed from the first stoker 309. The second stocker 329 is realized by, for example, a general tank or the like similar to the first stocker 309.

The mixing device 330 is arranged on the second pipeline 327 so that the taking-out line 327a is connected to an inlet of the mixing device 330 and the return line 327b is connected to an outlet thereof. The mixing device 330 mixes two or more stored powder extracts to produce a mixed extract. The produced mixed extract is conveyed to the first stocker 309 through the return line 327a.

The evaluating line 306 includes a sampler 341, a chromatographic device 343, and an evaluating device 10 and is configured to evaluate or examine whether a powder extract or a mixed extract in the first stocker 309 meets the criteria for productization.

The sampler 341 is arranged accessibly to the first stocker 309 and the chromatographic device 343. The sampler 341 obtains a sample of the powder extract or the mixed extract from the first stocker 309 and supplies the sample to the chromatographic device 343. According to the embodiment, the sampler 341 is realized by, for example, a powder sampler or the like that is driven by an actuator (not illustrated).

The chromatographic device 343 subjects the sample of the powder or mixed extract to high performance liquid chromatograph (HPLC) to prepare and obtain a three-dimensional chromatogram (3D chromatogram). The chromatographic device 343 is realized by a commercially-available device such as "Agilent 1100 system" manufactured by Agilent Technologies, or the like. Furthermore, the chromatography is not limited to the HPLC, and any other type of chromatography may be employed. The chromatographic device 343 is connected to the evaluating device 10 through a data line D and outputs the prepared 3D chromatogram to the evaluating device 10.

The evaluating device 10 has a function to evaluate or determine whether the powder or mixed extract meets the criteria for productization based on the input 3D chromatogram. The details of the evaluating device 10 will be explained later. The evaluating device 10 is connected to the control unit 308 through a data line D and outputs the determination or evaluating result to the control unit 308.

The control unit 308 is configured by a computer and controls each part of the formulating apparatus 301. According to the embodiment, the control unit 308 is a discrete unit separated from the evaluating device 10. The control unit 308 and the evaluating device 10, however, may be configured by a single unit.

The control unit 308 of this embodiment is connected to a sensor 309a of the first stocker 309, the sampler 341, the blowers 325, 331, 333 and 335, and the valves 337 and 339 through data lines D, respectively.

Then, the control unit 308 automatically causes the evaluating device 10 to evaluate whether the powder extract (or mixed extract) meets the criteria for productization, the dosage form processing device 311 to make the powder extract (or mixed extract) into the granules and the packing device 313 to pack the granules.

In particular, the control unit 308 determines a conveying state of the powder extract to the first stocker 309 based on a detecting signal sent from the sensor 309a of the first stocker 309. The sensor 309a is for example a load cell to detect the weight of the first stocker 309 and output the detecting signal to the control unit 308. The sensor 309a may be a flowmeter or the like.

The determination of the conveying state is performed by, for example, monitoring the rate of change of the weight of the first stocker 309. If the rate of change of the weight becomes zero, it can be determined that the conveying of the powder extract is completed. If the rate of change of the weight is reduced, it can be determined that the conveying of the powder extract approaches completion. The sensor may be provided to the extract producing device 307 to determine a producing state of the powder extract.

According to the conveying state of the powder extract, the control unit 308 controls the sampler 341 to feed the sample of the powder extract to the chromatographic device 343. The feeding of the sample can be performed whenever a conveyed amount of the powder extract in the first stocker 309 is sufficient to obtain the sample.

Further, the control unit 308 causes the first pipeline 323 to convey the powder extract from the first stocker 309 to the dosage form processing device 311 or one of the second stockers 329 based on the determination or evaluating result sent from the evaluating device 10.

In particular, if the evaluating device 10 determines that the powder extract meets the criteria for productization, the control unit 308 controls the first pipeline 323, in particular the blower 325 to convey the powder extract from the first stocker 309 to the dosage form processing device 311.

If the evaluating device 10 determines that the powder extract does not meet the criteria for productization, the control unit 308 controls the second pipeline 327, in particular the blower 331 and the valves 337 to convey the powder extract from the first stocker 309 to an empty one of the second stockers 329 and store the same. The determination whether the second stockers 329 are empty may be performed on the basis of detecting signals sent from sensors such as load cell provided to the respective second stockers 329.

Further, the control unit 308 controls the second pipeline 327, in particular the valves 337 and 339 and the blower 333 to convey two or more stored powder extracts in the second stockers 329 to the mixing device 330 and mix the same.

The mixing is initiated at any time during the first stocker 309 is empty. It, however, is required that the extract producing device 307 does not start to produce the next powder extract. The determination of whether the first stocker 309 is empty can be conducted based on the detecting signal from the sensor 309a.

The selection of powder extracts to be mixed and the mixing rate is based on MD value. As explained later, the evaluation of the powder extract finds a MD value using MT method and determines that a powder extract meets the criteria for productization if the found MD value is equal to or less than a threshold value. According to the embodiment, the powder extracts to be mixed and the mixing rate are determined using the MD values and mixes the determined powder extracts with the determined mixing rate to produce a mixed extract having a MD value being equal to or less than the threshold value.

After producing the mixed extract, the control unit 308 controls the second pipeline 327, in particular the blower 335 to convey the mixed extract from the mixing device 330 to the first stocker 309 and store the same. In response to the storage of the mixed extract, the control unit 308 controls the sampler 341 to feed the sample of the mixed extract to the chromatographic device 343.

As a result, the evaluating device 10 outputs the determination or evaluating result to the control unit 308. The control unit 308 conveys the mixed extract from the first stocker 309 to the dosage form processing device 311 or one of the second stockers 329 in the same way as the aforementioned powder extract.

Figure 19:
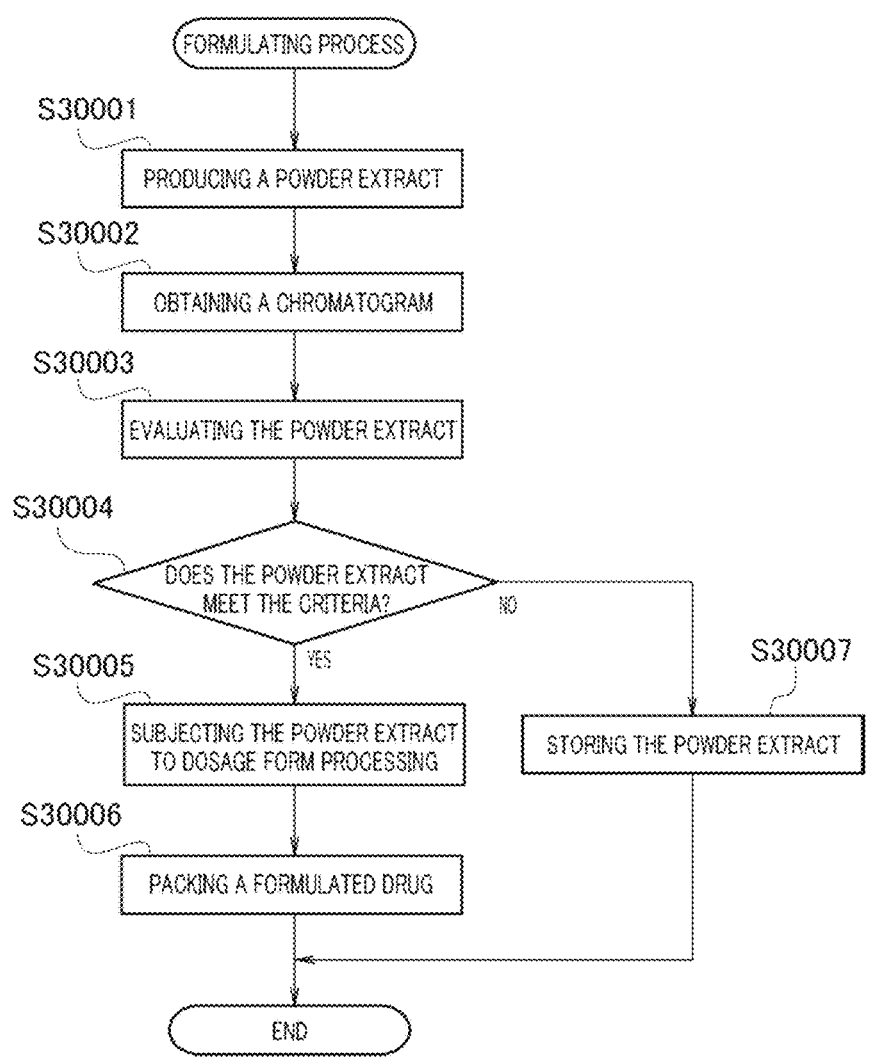
FIG. 19 is a flowchart illustrating a formulating process of a formulating method according to the first embodiment.

FIG. 19 is a flowchart illustrating a formulating process of a formulating method according to the first embodiment.

The formulating process of the formulating method of the first embodiment is started by putting the raw material crude drug into the extractor 315 of the extract producing device 307.

First, in Step S30001, a powder extract is produced. Namely, the extract producing device 307 extracts an essence as a liquid extract or an extraction liquid from the raw material crude drug at the extractor 315, subjects the extraction liquid to the solid-liquid separation at the separator 317, concentrates the extraction liquid to produce a concentrated liquid at the concentrator 319, and dries the concentrated liquid to make the same into a powder extract at the dryer 321 in sequence.

In Step S30002, a chromatogram is obtained. Namely, the powder extract produced in Step S30001 is conveyed from the extract producing device 307 to the first stocker 309 and is accommodated in the first stocker 309.

At this time, the control unit 308 causes the sampler 341 to obtain a sample of the powder extract and feed the obtained sample to the chromatographic device 343 according to the conveying state of the powder extract to the first stocker 309. The chromatographic device 343 subjects the fed sample to the HPLC to prepare a 3D chromatogram (FIG. 14).

In Step S30003, the powder extract is evaluated. Namely, the chromatographic device 343 outputs the 3D chromatogram obtained in Step S30002 to the evaluating device 10. As explained later, the evaluating device 10 evaluates or determines whether the powder extract meets the criteria for productization based on the input 3D chromatogram.

Namely, the evaluating device 10 selects the reference FP 55 according to the flowchart of FIG. 11, conducts the peak assignment of the target FP 43 to the selected reference FP 55, and assigns based on the peak assignment the peaks of the target FP 43 to the respective peaks of the reference group FP 18 as illustrated in FIGS. 16 and 17. Then, MT method is applied to the assigning result to find a MD value and it is determined that the powder extract meets the criteria for productization if the found MD value is equal to or less than threshold value.

In Step S30004, the formulating process is branched according to the evaluation of the powder extract. Namely, the evaluating device 10 outputs the determination or evaluating result of Step S30003 to the control unit 308. If the powder extract meets the criteria for productization, the control unit 308 transfers the formulating process to Step S30005. If the powder extract does not meet the criteria, the control unit 308 transfers the formulating process to Step S30007.

In Step S30005, the powder extract is subjected to the dosage form processing. Namely, the control unit 308 controls the blower 325 to convey the powder extract determined as an accepted one meeting the criteria to the dosage form processing device 311. Accordingly, the dosage form processing device 311 subjects the powder extract to the dosage form processing to produce a formulated drug, in particular granules in this embodiment.

In Step S30006, the formulated drug is packed. Namely, the granules produced in Step S30005 are subdivided and packed at the packing device 313. In this way, the productization of the powder extract is completed and the formulating process is terminated.

On the other hand, in Step S30007, the powder extract is stored. Namely, the control unit 308 controls the blower 331 and the valve 337 to convey the powder extract determined as a rejected one that does not meet the criteria to an empty one of the second stockers 329 and store that powder extract.

With this, the formulating process is terminated without producing granules for the powder extract that does not meet the criteria. At this time, the MD value of the powder extract used in the determination or evaluation of the stored powder extract is registered in a database or the like.

Figure 20:
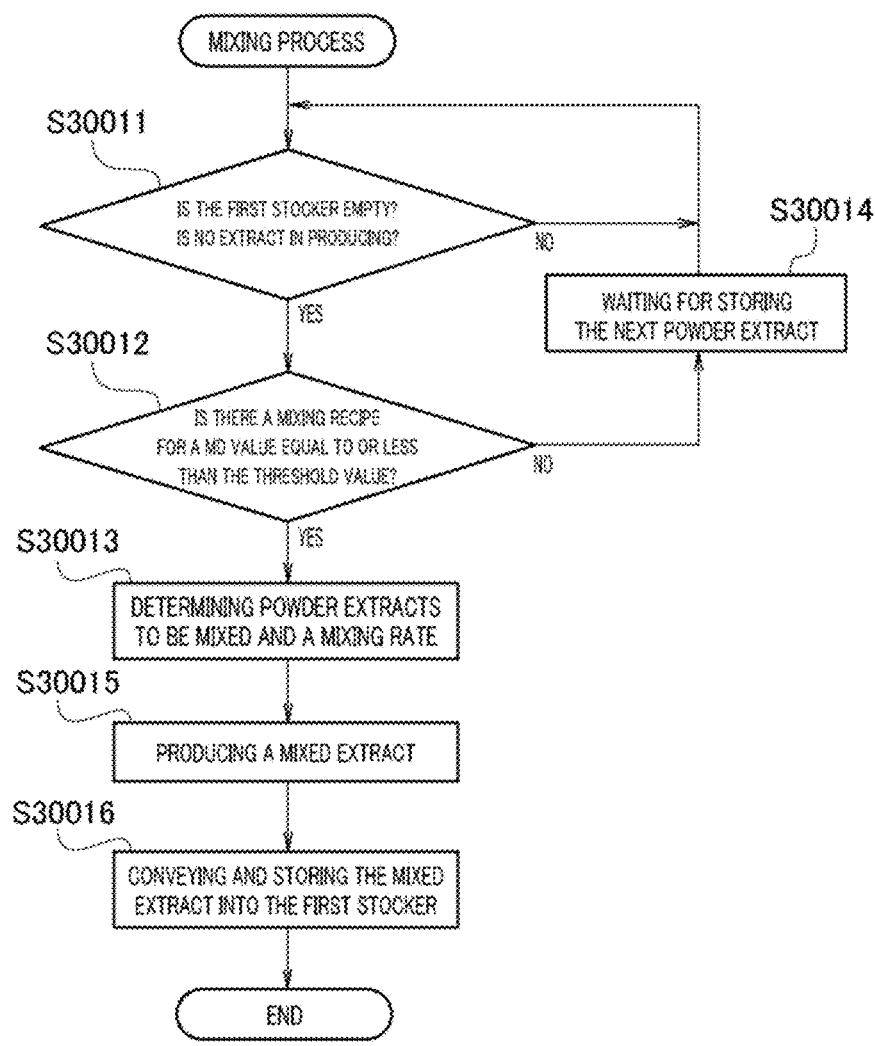
FIG. 20 is a flowchart illustrating a mixing process of the formulating method according to the first embodiment.

FIG. 20 is a mixing process of the formulating method according to the first embodiment.

The mixing process of the formulating method of the first embodiment is started by storing two or more powder extracts in the second stockers 329.

In Step S30011, it is determined whether the first stocker 309 is empty and no extract is in producing. Namely, the control unit 308 determines whether the first stocker 309 is empty and no extract is producing based on the detecting signal of the sensor 309a. The presence or absence of an extract in producing may be more correctly determined in view of an operating signal of the extract producing device 307.

The control unit 309 transfers the mixing process to Step S30012 if the first stocker 309 is empty and no extract is in producing, and repeats Step S30011 otherwise.

In Step S30012, it is determined whether there is a mixing recipe for the stored powder extracts in the second stockers 329 capable of forming a mixed extract having a MD value being equal to or less than the threshold value.

Namely, the control unit 308, in the case where two or more powder extracts to be mixed are selected from among the stored powder extracts based on the MD values and the selected powder extracts are mixed, determines whether there is a combination and a mixing rate of two or more stored powder extracts to be mixed as a mixing recipe capable of forming a mixed extract having a MD value being equal to or less than the threshold value. The MD values for the determination may be obtained from the database or the like.

The control unit 308 transfers the mixing process to Step S30013 if there is such a mixing recipe, and to Step S30014 otherwise.

In Step S30013, a combination and a mixing rate of powder extracts to be mixed are determined. Namely, the control unit 308 determines the powder extracts to be mixed and the mixing rate based on the mixing recipe of Step S30012.

In Step S30014, it waits for storing the next powder extract. Namely, the control unit 308 cannot produce a mixed extract having a MD value being equal to or less than the threshold value from the presently stored powder extracts and waits until the next powder extract is stored.

In Step S30015, a mixed extract is produced using the determined combination and mixing rate of the powder extracts to be mixed. Namely, the control unit 308 controls the valves 337 corresponding to the second stockers 329 storing the powder extracts to be mixed, the valve 339 and the blower 333 for the mixing device 330 to convey the powder extracts to be mixed to the mixing device 330. As the control of the valves 337, 339 and the blower 333, the control unit 308 controls the open time of the valves 337 and the operating time of the blower 333 to adjust the amount of the powder extracts to be conveyed according to the mixing rate. As a result, the mixing device 330 produces the mixed extract using the combination and the mixing rate of the powder extract determined in Step S30013.

In Step S30016, the mixed extract is conveyed to and stored in the first stocker 309. Namely, the control unit 308 controls the blower 335 to convey the produced mixed extract to the first stocker 309 and accommodate the same in the first stocker 309.

In this way, the mixing process is terminated. Thereafter, the formulating method performs for the mixed extract Step S30002 and the following steps of the formulating process of FIG. 19 in sequence. Accordingly, if the mixed extract is determined as an accepted one meeting the criteria for productization, granules are produced from the mixed extract and packed. On the other hand, if the mixed extract is determined as a rejected one that does not meet the criteria for productization, the mixed extract is stored in an empty one of the second stockers 329 again. The mixed extract, however, is produced so as to meet the criteria and therefore the latter case is extremely rare. With this, in the formulating process for the mixed extract, the evaluation of whether the mixed extract meet the criteria may be omitted.

As mentioned above, the first embodiment of the invention is the formulating method, when evaluating similarity between the target FP 15 and the reference FP 17, in which a plurality of peaks (19, 21, . . . ) and (39, 41, . . . ) are collected, performs the patterning step S1 of patterning each of the peaks (19, 21, . . . ) and (39, 41, . . . ) of the target FP 15 and the reference FP 17 with the appearance distance as illustrated in FIGS. 5 and 6, the matching number extraction step S2 of comparing each patterned pattern in a round-robin to find the numbers of matches as illustrated in FIG. 8, and the matching degree determination step S3 of finding the degree of matching as illustrated in FIG. 9 with the use of Tanimoto coefficient on the basis of the found numbers of matches.

It, therefore, is possible to evaluate similarity between the target FP 15 and the reference FP 17 simply and quickly, thereby selecting the reference FP 55(17) that is similar to the target FP 43(15) in the FP pattern as much as possible from among the plurality of reference FP based on the similarity evaluation and assigning each peak of the target FP 43(15) to a corresponding peak of the selected reference FP 55(17) with high accuracy In this way, the embodiment improves the accuracy of the peak assignment of the target FP 43 which is conducted to the selected reference FP 55, thereby improving the accuracy of the evaluation in comparison of the target FP 43 and the reference FP 55 and therefore the accuracy of the evaluation of whether the powder extract of the multicomponent drug meets the criteria for productization.

As a result, the present invention surely subjects a powder extract of a multicomponent drug determined as an accepted one meeting the criteria for productization with high accuracy to the dosage form processing to make the powder extract into a product. This reduces the variation in multicomponent drugs to be subjected to the dosage form processing and realizes the high quality of the products.

In the matching degree determination step S3, Tanimoto coefficient is set as $T=c/(a+b-c)$ in which "a" is the number of the peaks of the target fingerprint, "b" is the number of the peaks of the reference fingerprint, and "c" is the number of matches in any one of the appearance distance, height ratio and area ratio, to find the degree of matching expressed by $D=(1-T)$ and being closer to zero. According to the embodiment, the degree of matching D is weighted by $(a-c+1)$ being equal to d, which when combined becomes D×d to find the degree of matching.

Accordingly, it is possible to select a reference FP that matches more to the peaks (19, 21, . . . ) of the target FP 15 due to the weighting.

Further, the embodiment mixes the powder extract of the multicomponent drug determined as a rejected one that does not meet the criteria for productization with one or more other powder extracts that do not meet the criteria for productization to form a mixed extract without subjecting the evaluated powder extract to the dosage form processing, evaluates whether the mixed extract meets the criteria for productization, and subjects the mixed extract determined as an accepted one meeting the criteria for productization to the dosage form processing.

Thus, even the powder extract that does not meet the criteria for productization is made into a product by mixing with the other powder extracts.

According to the embodiment, comparing and evaluating the target FP integrated feature values and reference FP integrated feature values finds a MD value using the MT method and evaluates the powder extract of which MD value is equal to or less than the threshold value as the accepted one.

With this, the embodiment conducts the evaluation of whether the powder extract meets the criteria for productization with higher accuracy.

Furthermore, the producing of a mixed extract uses MD values to determine a mixing rate of powder extracts to be mixed and mixes the powder extracts with the determined mixing rate to form the mixed extract having a MD value that is equal to or less than the threshold value.

Accordingly, the embodiment surely produces the mixed extract having the MD value that is equal to or less than the threshold value, i.e., meeting the criteria for productization and therefore improves the accuracy and the efficiency of the productization of the mixed extract of the multicomponent drug.

According to the formulating device 301 of the first embodiment of the invention, it is possible to realize the formulating method by operating each part of the evaluating device 10.

According to the embodiment, the formulating apparatus 301 includes the extract producing device 307 extracting an essence from a raw material crude drug to produce a powder extract of a multicomponent drug, the first pipeline 323 led from the extract producing device 307 to the dosage form processing device 311, the first stocker 309 arranged on the first pipeline 323 to accommodate the produced powder extract, the sampler 341 obtaining a sample from the powder extract accommodated in the first stocker 309 and feeding the obtained sample to the chromatographic device 343, and the control unit 308 controlling the sampler 341 to feed the sample to the chromatographic device 343 and then controlling the first pipeline 323 to convey the powder extract from the first stocker 309 to the dosage form processing device 311 in response to a determination made at the evaluating device 10 that the powder extract meets the criteria for productization.

The formulating apparatus 301 of this embodiment automatically conducts the formulating process in which the powder extract is produced from the raw material crude drug and the powder extract meeting the criteria for productization is subjected to the dosage form processing. Further, the pipeline 323 is extended from the dosage form processing device 311 to the packing device 313 and automatically conducts also the packing of the formulated drug subsequent to the dosage form processing.

The formulating apparatus 301 includes the second pipeline 327 led from and back to the first stocker 309, and the second stockers 329 arranged on the second pipeline 327 for accommodating powder extracts that do not meet the criteria for productization. The control unit 308 controls the second pipeline 327 to convey that powder extract from the first stocker 309 to an empty one of the second stokers 329 in response to a determination made at the evaluating device 10 that the powder extract does not meet the criteria for productization.

Accordingly, the formulating apparatus 301 automatically stores the produced powder extract without the dosage form processing if that powder extract does not meet the criteria for productization.

The formulating apparatus 301 includes the mixing device 330 arranged on the second pipeline 327. The control unit 308 controls the second pipeline 327 to convey two or more powder extracts accommodated in the second stockers 329 to the mixing device 330 at which the conveyed extracts are mixed to form the mixed extract and to convey the mixed extract from the mixing device 330 to the first stocker 309 at which the mixed extract is accommodated and then controls the sampler 341 to feed the sample of the mixed extract to the chromatographic device 343.

Accordingly, the formulating apparatus 301 automatically conducts the evaluation of whether the produced mixed extract meets the criteria for productization and automatically subjects the mixed extract to the dosage form processing or store the mixed extract according to the evaluation.

In addition, the formulating apparatus 301 realizes the formulating method to obtain the same effects as the formulating method.

Figure 10:
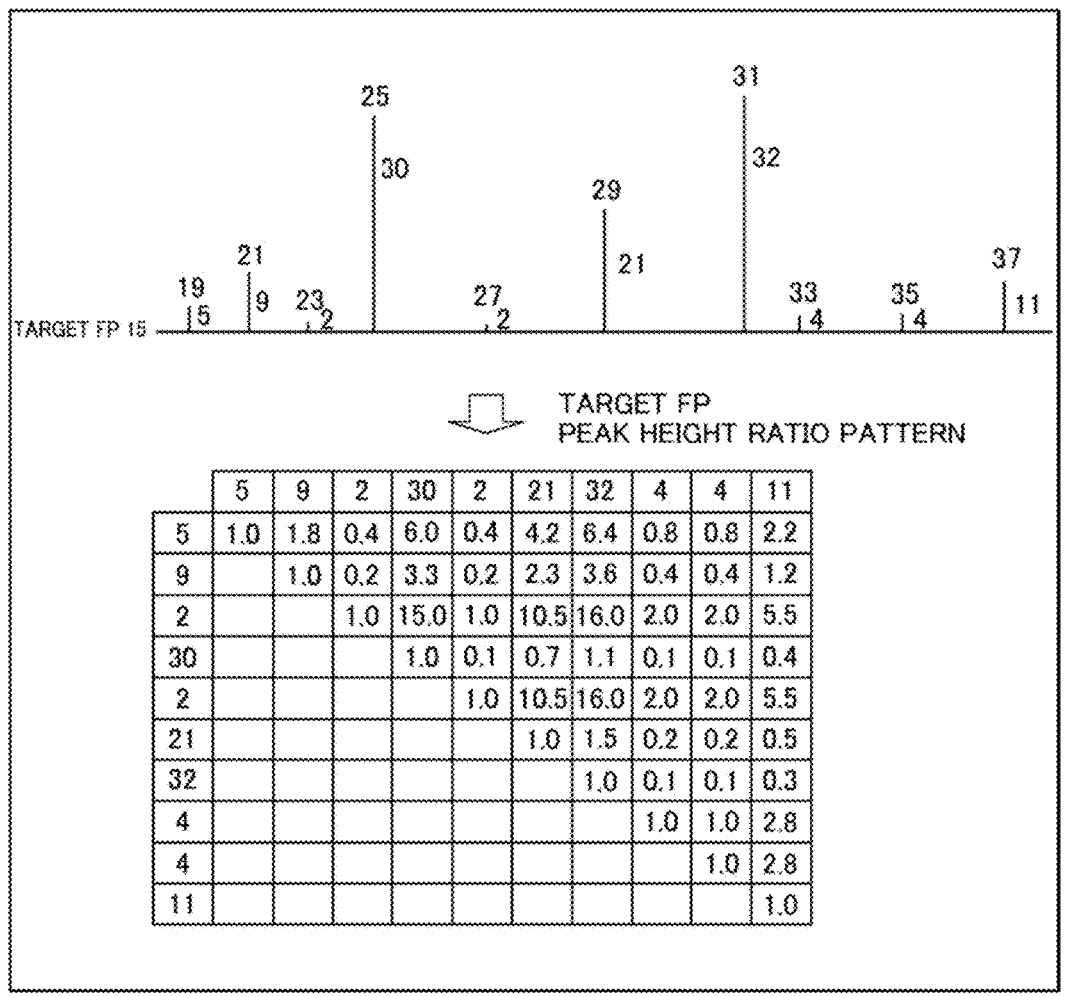
FIG. 10 is an explanatory diagram illustrating a peak height ratio pattern of the target FP according to a second embodiment.

FIG. 10 is an explanatory diagram illustrating a peak height ratio pattern of a target FP according to the second embodiment.

In Embodiment 2, the target FP 15 in the upper side of FIG. 10 is patterned in the form of a table in which value of each cell is a peak height ratio as illustrated in the lower side.

In FIG. 10, the peak heights of respective peaks (19, 21, 23, 25, 27, 29, 31, 33, 35, 37) of the target FP 15 are (5, 9, 2, 30, 2, 21, 32, 4, 4, 11).

Therefore, the height ratio between the peak 19 and the peak 21 is (9÷5)=(1.8). Similarly, the height ratio between the peak 19 and the peak 23 is (0.4), the height ratio between the peak 21 and the peak 23 is (0.2), and the like. The followings are similar, and the height ratio pattern of the target FP is acquired as illustrated in the lower side of FIG. 10.

Also for the reference FPs, the height ratio patterns of the peaks of the reference FPs are acquired similarly.

Therefore, in Embodiment 2, the patterning step S1 performs patterning with the height ratio for the peaks as a scale.

In the matching number extraction step S2, the number of matches in the height ratio is set as the matching number, and each patterned peak with the height ratio of the peak is compared in a round-robin, to calculate the number of the height ratio matching within a set range. From this calculation, it is possible to obtain the matching number similarly to FIG. 8.

In addition, this embodiment of patterning with the height ratio of the peak may have a plurality of identical values in a single row illustrated in the lower side of FIG. 10 and there is a need not to count these values a plurality of times.

The matching degree determination step S2 sets Tanimoto coefficient as T=c/(a+b−c) in which "a" is the number of the peaks of the target fingerprint, "b" is the number of the peaks of the reference fingerprint, and "c" is the number of matches in height ratio, to find the degree of matching expressed by D=(1−T) and being closer to zero.

Further, the degree of matching D is weighted by d being equal to (a−c+1), which when combined becomes D×d in order to find the degree of matching, to select a reference FP whose peaks matche more to the peaks (19, 21, . . . ) of the target FP 15 due to the weighting.

Therefore, the second embodiment can provide similar effects to those of the first embodiment.

Figure 21:
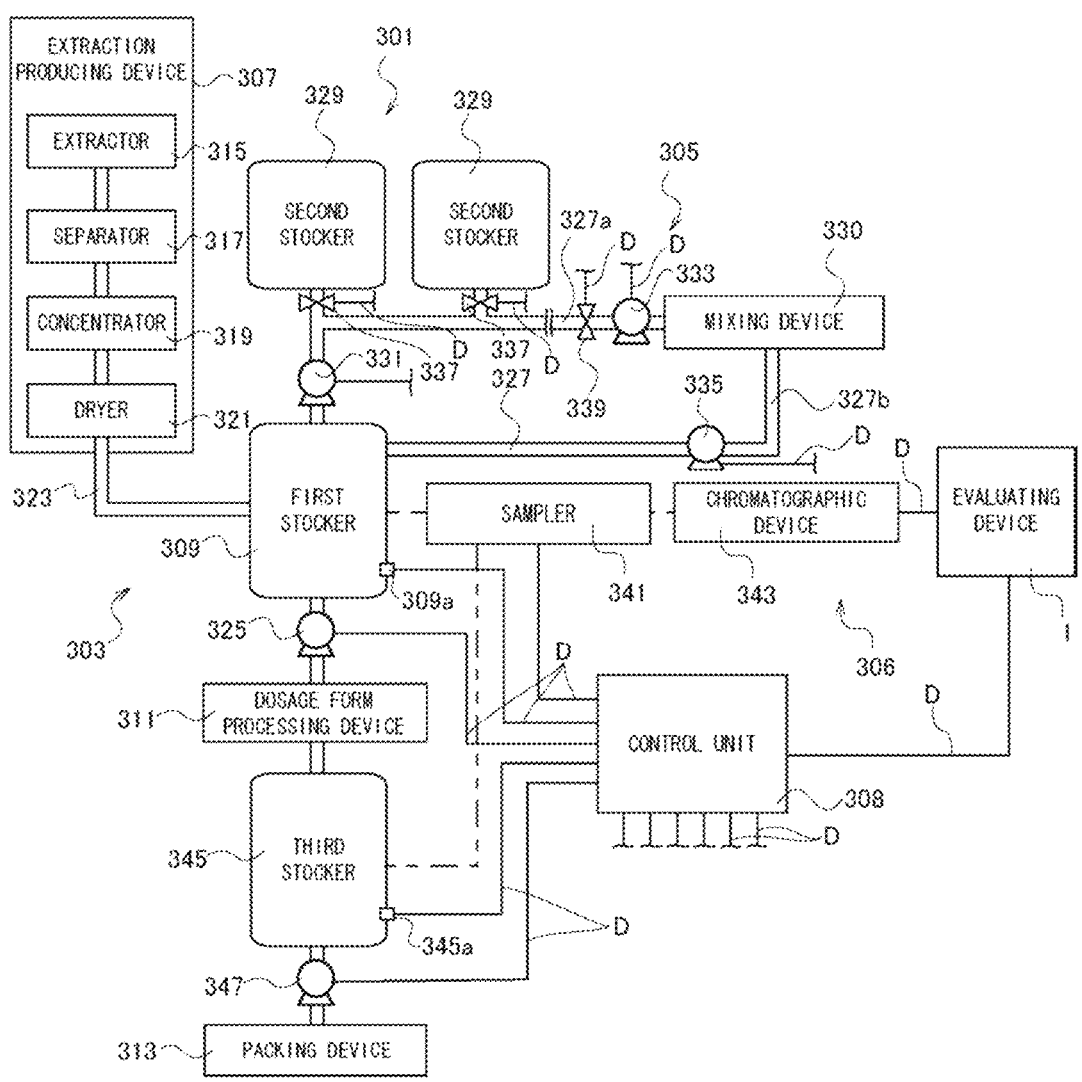
FIG. 21 is a schematic block diagram illustrating a formulating apparatus according to a third embodiment of the present invention.

FIG. 21 is a schematic block diagram illustrating a formulating apparatus according to the third embodiment of the present invention. The third embodiment has the same basic structure as the first embodiment and therefore corresponding parts are represented with the same reference numerals to omit the repetition in the explanation.

The formulating apparatus 301 according to the third embodiment further includes a third stocker 345 and a blower 347 in comparison with the first embodiment of FIG. 18. The third stocker 45 is arranged or laid downstream of the dosage form processing device 311 on the first pipeline 323. The blower 347 is arranged downstream of the third stocker 345 on the first pipeline 323.

According to the embodiment, the formulating apparatus 301 accommodates in the third stocker 345 granules produced through the dosage form processing at the dosage form processing device 311, evaluates whether the granules meet the criteria for productization at the evaluating device 10, and conveys the granules determined as accepted ones meeting the criteria for productization to the packing device 313 using the blower 347.

The third stocker 345 is a general tank or the like similar to the first stocker 309. The third stocker 345 includes a sensor 345a. The sensor 345a is a load cell or the like similar to the sensor 309a of the first stocker 309.

According to the embodiment, the control unit 308 determines a conveying state of the granules to the third stocker 345 according to the detecting signal from the sensor 345a of the third stocker 345. Then, the control unit 308 controls the sampler 341 according to the conveying state to obtain the sample of the granules stored in the third stocker 345 and feed the obtained sample to the chromatographic device 343.

In response to the feeding, the chromatographic device 343 obtains a 3D chromatogram and outputs the same to the evaluating device 10, and the evaluating device 10 evaluates whether the granules meet the criteria for productization based on the chromatogram and outputs the evaluating result to the control unit 308.

The control unit 308 controls the blower 345 to convey the granules from the third stocker 345 to the packing device 313 in the case where the granules meet the criteria for productization according to the evaluating result.

The third embodiment, therefore, conclusively confirms that the granules meet the criteria after producing the granules and before packing the same. This allows only the granules meeting the criteria to be surely packed.

This embodiment is particularly advantageous for production of the granules from the mixed extract. Namely, the mixed extract of the embodiment is produced to meet the criteria for productization and therefore it is not required to evaluate whether the mixed extract accommodated in the first stocker 309 meets the criteria.

Accordingly, the third embodiment conclusively confirms that the granules stored in the third stocker 345 meet the criteria without confirmation for the mixed extract stored in the first stocker 309, to omit repeated evaluation and improve the efficiency for productization.

In addition, the third embodiment obtains the same effects as the first embodiment.

Figure 22:
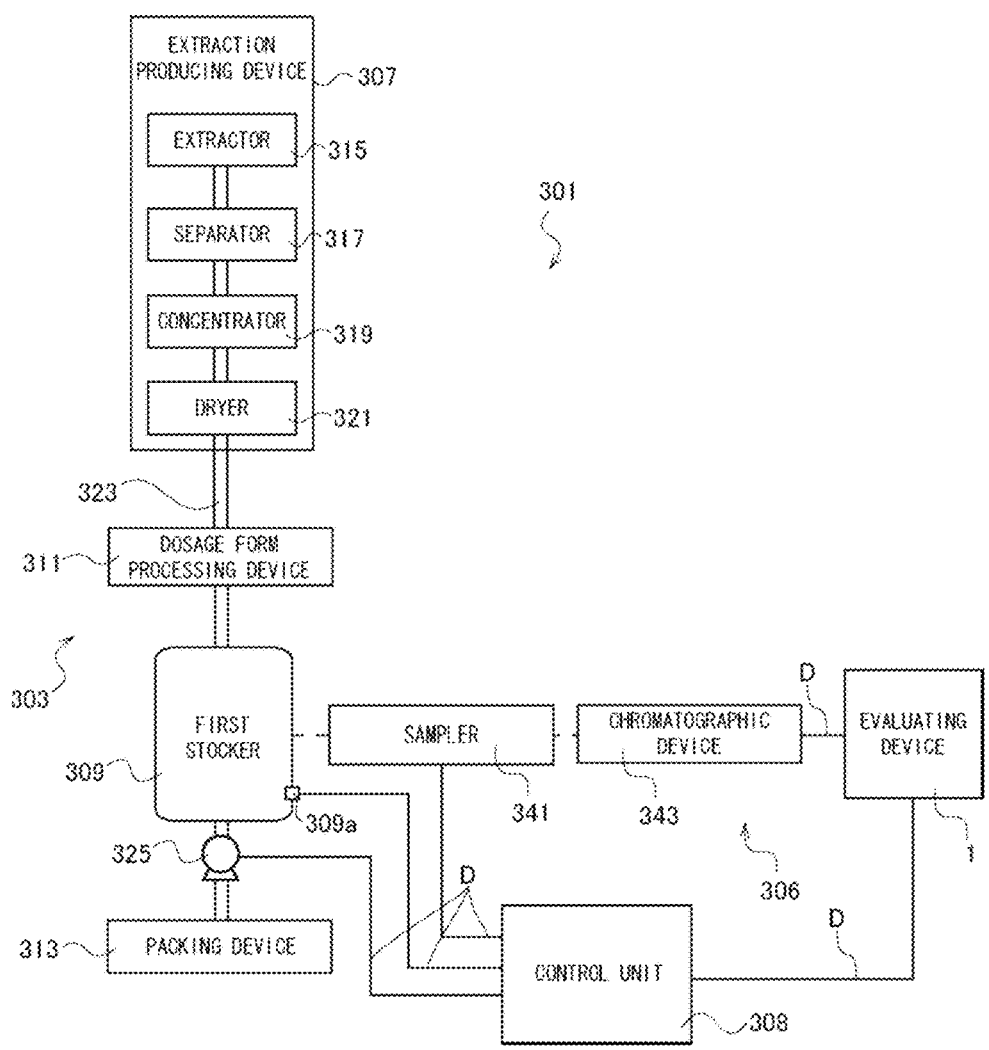
FIG. 22 is a schematic block diagram illustrating a formulating apparatus according to a fourth embodiment of the present invention.

FIG. 22 is a schematic block diagram illustrating a formulating apparatus according to the fourth embodiment of the present invention. The fourth embodiment has the same basic structure as the first embodiment and therefore corresponding parts are represented with the same reference numerals to omit the repetition in the explanation.

The formulating apparatus 301 according to the embodiment conducts evaluation of granules without conducting evaluation of a powder extract.

For this, the dosage form processing device 311 is arranged or laid downstream of the extraction producing device 307 and a powder extraction produced at the extract producing device 307 is conveyed to the dosage form processing device 311 through the first pipeline 323 to produce granules.

On the downstream side of the dosage form processing device 311, the first stocker 309 is arranged to accommodate the granules. To the granules accommodated in the first stocker 309, the evaluating line 306 evaluates whether to meet the criteria for productization.

The evaluating result or determination is input to the control unit 308 and the control unit 308 controls the blower 325 to convey the granules from the first stocker 309 to the packing device 313 in the case where the granules meet the criteria for productization. The packing device 313 subdivides and packs the conveyed granules.

The fourth embodiment, therefore, packs granules meeting the criteria for productization and does not pack granules not meeting that criteria based on the high-accuracy evaluation at the evaluating device 10, thereby to surely pack the granules for the multicomponent drug meeting that criteria to make the same into a product. Although the embodiments of the present invention are applied to evaluation of the kampo medicine as a multicomponent drug, the present invention may be applied to evaluation of other multicomponent materials. The chromatogram is not limited to the 3D chromatogram, and a FP may be used as what composed of peaks with the exclusion of UV spectra and of retention time points thereof.

The FP of the aforementioned embodiments is prepared on the basis of the peak heights (maximum values in signal strength), to be evaluated similarity by the aforementioned method. However, even when a FP is prepared with area values of peaks, the FP can be evaluated in the same way.

That is, peaks used in the similarity evaluating method, the similarity evaluating program and the similarity evaluating device for collective data according to the present invention encompasses a case where a peak means the maximum value of signal intensity (height) as described above and also a case where a peak means an area value of signal intensity (peak area) is expressed as the height.

In this case, even when a FP is prepared with the peak areas, the FP is prepared by expressing the peak areas as heights. As the FP, it is a similar expression to the case where the FP is prepared with the peak heights of the aforementioned embodiment. Consequently, even if the FP is prepared with the peak areas, it is possible to evaluate similarity by the process of the aforementioned the first to fourth embodiments in the same way as the case where the FP is prepared with the peak heights of signal strength or intensity.

Therefore, the invention may employ area ratio of the peak area as a scale other than the peak appearance distance of the first embodiment and the peak height of the second embodiment.

What is claimed is:

1. A method of formulating a multicomponent drug, comprising:

obtaining, with chromatography equipment and a first processor, a chromatogram from a base of the multicomponent drug;

evaluating, with second processor, whether the base meets criteria for productization by evaluating fingerprints based on the obtained chromatogram; and if the base meets the criteria for productization, subjecting, under control of a third processor, the base to productization using a dosage form processing at a dosage form processing device, to produce a formulated drug having a given dosage-form, wherein the evaluating, with the second processor, whether the base meets the criteria for productization by evaluating the fingerprints based on the obtained, chromatogram comprises:

gathering, as a target fingerprint, peaks where a peak is defined by at least a local maximum or an area value in signal strength and a retention time point from the chromatogram;

patterning, with a selected scale that is any one of an appearance distance or a ratio in the local maximum value or the area value in signal strength, each peak of the target fingerprint and reference fingerprints, the reference fingerprints each comprising peaks where a peak is defined by at least a local maximum or an area value in signal strength and a retention time point from a chromatogram of a multicomponent drug that is determined as a normal product, the patterning of each peak of the target fingerprint and the reference fingerprints conducted by obtaining values of the selected scale between a peak to be patterned and peaks excluding antecedent peaks which are antecedent to the peak to be patterned in retention time order and forming a respective matrix for each of the reference fingerprints and for the target fingerprint wherein each element of each of the matrixes is a respective one of the obtained values of the selected scale;

comparing the obtained values in a corresponding row of the matrix for the target fingerprint and of the matrix for each of the reference fingerprints row-by-row in a round-robin sequence to find numbers of matches in the values of the selected scale;

finding a degree of matching between the target fingerprint and said each one of the reference fingerprints with use of Tanimoto coefficient on the basis of the found numbers of matches in the values of the selected scale to evaluate similarity between the target fingerprint and each one of the reference fingerprints;

selecting one of the reference fingerprints based on the similarity; and assigning the peaks of the target fingerprint to peaks of the selected one of the reference fingerprints to deters nine whether the base is an accepted one that meets the criteria for productization; and wherein:

the base which meets the criteria for productization and is subjected, under the control of the third processor, to the productization using the dosage form processing at the dosage form processing device to produce the formulated drug having the given dosage-form, is the base which is the accepted one according to the determining of the accepted one.

2. The method according to claim 1, wherein
the Tanimoto coefficient is expressed by $T=c/(a+b-c)$ in which
"a" is the number of the peaks of the target fingerprint,
"h" is the number of the peaks of the reference fingerprint,
"c" is the number of matches the values of the selected scale, and
the degree of matching is expressed by $D=(1-T)$, and the closer to zero the degree of matching, the higher the similarity.

3. The method according to claim 2, wherein
D is weighted by d, where d is equal to $(a-c+1)$, which when D is combined with d yields a weighted degree of matching.

4. The method according to claim 1, further comprising:
if the base is a rejected one that does not meet the criteria for productization, mixing, under the control of the third processor, the base with one or more other bases that are rejected ones and do not meet the criteria for productization using a mixing mechanism to form a mixed base without subjecting the evaluated base to the dosage form processing;
obtaining a chromatogram from the mixed base with the chromatography equipment and the first processor;
determining, with the second processor whether the mixed base is an accepted one that meets the criteria for productization based on the obtained chromatogram; and if the mixed base is the accepted one according to the determining of the accepted one, subjecting, under the control of the third processor, the mixed base to productization using the dosage form processing at the dosage form processing device.

5. The method according to claim 1, wherein
evaluating, with the second processor, whether the base meets the criteria for productization includes finding a Mahalanobis distance of the target finger print relative to a unit space representing the reference fingerprints using a Mahalanobis-Taguchi method and determining the base as the accepted one if the base has the Mahalanobis distance being equal to or less than a predetermined threshold value.

6. The method according to claim 5, further comprising:
mixing the base with one or more other bases that are the rejected ones includes determining, with the third processor, a mixing rate that is a ratio of quantities of the bases to be mixed based on the Mahalanobis distances of the bases to be mixed and mixing, under the control of the third processor, the bases to be mixed at the determined mixing rate using the mixing mechanism to form the mixed base having a Mahalanobis distance that is equal to or less than the predetermined threshold value.

7. An apparatus for formulating a multicomponent drug, comprising:
chromatography equipment and a first processor obtaining a chromatogram from a base of the multicomponent drug;
a second processor connected to the first processor via a data line and obtaining the chromatogram from the first processor;
a dosage form processing device subjecting the base to productization using a dosage form processing, to produce a formulated drug having a given dosage form; and
a third processor connected to the second processor via a data line and causing the dosage form processing device to perform the dosage form processing of the base if the base meets the criteria for productization, wherein
the second processor is programmed to:
gather from the obtained chromogram, as a target fingerprint, peaks where a peak is defined by at least a local maximum or an area value in signal strength and retention time point from the chromatogram;
pattern, with a selected scale that is any one of an appearance distance or a ratio in the local maximum value or the area value in signal strength, each peak of the target fingerprint and reference fingerprints, the reference fingerprints each comprising peaks where a peak is defined by at least a local maximum or an area value in signal strength and a retention time point from a chromatogram of a multicomponent drug that is determined as a normal product, the patterning of each peak of the target fingerprint and the reference fingerprints conducted by obtaining values of the selected scale between a peak to be patterned and peaks excluding antecedent peaks which are antecedent to the peak to be patterned in retention time order and form a respective matrix for each of the reference, fingerprints and for the target fingerprint wherein each element of each of the matrixes is a respective one of the obtained values of the selected scale;

compare the obtained values in a corresponding row of the matrix for the target fingerprint and the matrix for each of the reference fingerprints row-by-row in a round-robin sequence to find numbers of matches in the value of the selected scale;

find a degree of matching between the target fingerprint and said each one of the reference fingerprints with use of Tanimoto coefficient on the basis of the found numbers of matches in the values of the selected scale to evaluate similarity between the target fingerprint and each one of the reference fingerprints;

select one of the reference fingerprints based on the degree of matching; and assign the peaks of the target fingerprint to peaks of the selected one of the reference fingerprints to determine whether the base is an accepted one that meets the criteria for productization; and the third processor is programmed to if determine that the base which is the accepted one according to the determining of the accepted one with the second processor is the base which meets the criteria for productization and is programmed to effect the causing the dosage form processing device to perform the dosage form processing of the base which meets the criteria for productization.

8. The apparatus according to claim 7, wherein the Tanimoto coefficient is expressed by $T=c/(a+b-c)$ in which
"a" is the number of the peaks of the target fingerprint,
"b" is the number of the peaks of the reference fingerprint,
"c" is the number of matches in the values of the selected scale, and
the degree of matching is expressed by $D=(1-T)$, and the closer to zero the degree of matching, the higher the similarity.

9. The apparatus according to claim 8, wherein D is weighted by d, where d is equal to $(a-c+1)$, which when D is combined with d yields a weighted degree of matching.

10. The apparatus according to claim 7, further comprising:
a mixing mechanism mixing bases to produce a mixed base, wherein
the third processor is programmed to, if the base is the rejected one, cause the mixing mechanism to mix the base with one or more other bases that are rejected ones and do not meet the criteria for productization to form a mixed base,
the first processor is programmed to obtain a chromatogram from the mixed base using the chromatography equipment,
the second processor is programmed to determine whether the mixed base is an accepted one that meets the criteria for productization based on the obtained chromatogram of the mixed base, and
the third processor is programmed to control that, if the mixed base is the accepted one, the mixed base is subjected to productization using the dosage form processing at the dosage form processing device.

11. The apparatus according to claim 7, wherein the second processor finds a Mahalanobis distance of the target fingerprint with respect to unit space representing the reference fingerprints using a Mahalanobis-Taguchi method and determines the base as the accepted one if the base has the Mahalanobis distance being equal to or less than a threshold value.

12. The apparatus according to claim 11, wherein the third processor is programmed to:
if the mixed base is the rejected one according to the determining of the accepted one, determine a mixing rate that is a ratio of quantities of the bases to be mixed based on the Mahalanobis distances of the bases to be mixed; and
cause the mixing mechanism to mix the bases to be mixed at the mixing rate to form the mixed base having a Mahalanobis distance that is equal to or less than the predetermined threshold value.

\* \* \* \* \*

UNITED STATES PATENT AND TRADEMARK OFFICE
CERTIFICATE OF CORRECTION

PATENT NO. : 10,533,979 B2  
APPLICATION NO. : 15/269644  
DATED : January 14, 2020  
INVENTOR(S) : Yoshikazu Mori et al.

Page 1 of 1

It is certified that error appears in the above-identified patent and that said Letters Patent is hereby corrected as shown below:

In the Claims

Claim 1, Column 26, Line 55:  
Change "... obtained, chromatogram ..." to --... obtained chromatogram ...--

Claim 1, Column 27, Line 30:  
Change "... deters nine ..." to --... determine ...--

Claim 2, Column 27, Line 43:  
Change "h ..." to --b ...--

Claim 7, Column 28, Line 45:  
Change "... chromogram, ..." to --... chromatogram, ...--

Claim 7, Column 28, Line 64:  
Change "... reference, fingerprints" to --... reference fingerprints ...--

Claim 7, Column 29, Line 18:  
Change "... to if determine ..." to --... to determine ...--

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*